United States Patent
Slynko et al.

(10) Patent No.: US 12,125,581 B2
(45) Date of Patent: Oct. 22, 2024

(54) MEDICAL IMAGING DATA COMPRESSION AND EXTRACTION ON CLIENT SIDE

(71) Applicant: Align Technology, Inc., San Jose, CA (US)

(72) Inventors: Yury Slynko, Moscow (RU); Vitaliy Vladimirovich Chernov, Moscow (RU); Ilya Baryshnikov, Belgorod Oblast (RU)

(73) Assignee: Align Technology, Inc., San Jose, CA (US)

( * ) Notice: Subject to any disclaimer, the term of this patent is extended or adjusted under 35 U.S.C. 154(b) by 281 days.

(21) Appl. No.: 17/182,190

(22) Filed: Feb. 22, 2021

(65) Prior Publication Data
US 2021/0265044 A1    Aug. 26, 2021

Related U.S. Application Data

(60) Provisional application No. 62/979,325, filed on Feb. 20, 2020.

(51) Int. Cl.
*G06K 9/00* (2022.01)
*A61C 9/00* (2006.01)
(Continued)

(52) U.S. Cl.
CPC .............. *G16H 30/40* (2018.01); *A61C 9/004* (2013.01); *G06T 5/40* (2013.01); *G06T 5/92* (2024.01);
(Continued)

(58) Field of Classification Search
CPC ..................... G16H 30/40; G16H 30/20; G06T 2207/10081; G06T 2207/30036;
(Continued)

(56) References Cited

U.S. PATENT DOCUMENTS 5,975,893 A    11/1999    Chishti et al.
6,227,850 B1    5/2001    Chishti et al.
(Continued)

FOREIGN PATENT DOCUMENTS

| JP | 2009291280 A | 12/2009 | |
| RU | 2595598 | * 11/2014 | ............... G06N 3/02 |
| RU | 2595598 C2 | * 8/2016 | |

OTHER PUBLICATIONS

Srivastava, Meenakshi, and Suneeta Agarwal. "Compression of medical images using their symmetry." 2018 5th IEEE Uttar Pradesh section international conference on electrical, electronics and computer engineering (UPCON). IEEE, Nov. 2018.*

(Continued)

*Primary Examiner* — Gregory A Morse
*Assistant Examiner* — Owais Iqbal Memon
(74) *Attorney, Agent, or Firm* — Shay Glenn LLP

(57) ABSTRACT

Apparatuses and computer-implemented methods for compression and extraction of three-dimensional (3D) volumetric imaging data, including in particular medical and dental imaging data, that may receive the 3D volumetric image data and preparing compressed 3D volumetric image data for compression by analyzing a relevant region of the 3D volumetric image data. The method may further include compressing, into compressed 3D volumetric image data, the pre-processed static 3D volumetric image data using a video compression scheme. Various other methods, systems, and computer-readable media are also disclosed.

29 Claims, 16 Drawing Sheets

(51) Int. Cl.

| | | |
|---|---|---|
| *G06T 5/40* | (2006.01) | |
| *G06T 5/92* | (2024.01) | |
| *G06T 7/11* | (2017.01) | |
| *G16H 30/20* | (2018.01) | |
| *G16H 30/40* | (2018.01) | |
| *H04N 19/176* | (2014.01) | |
| *H04N 19/625* | (2014.01) | |
| *H04N 19/91* | (2014.01) | |

(52) U.S. Cl.
CPC ............. *G06T 7/11* (2017.01); *G16H 30/20* (2018.01); *H04N 19/176* (2014.11); *H04N 19/625* (2014.11); *H04N 19/91* (2014.11); *G06T 2200/04* (2013.01); *G06T 2207/10016* (2013.01); *G06T 2207/10081* (2013.01); *G06T 2207/20052* (2013.01); *G06T 2207/20132* (2013.01); *G06T 2207/30036* (2013.01)

(58) Field of Classification Search
CPC ... G06T 5/009; G06T 5/40; G06T 7/11; G06T 2200/04; G06T 2207/10016; G06T 2207/20052; G06T 2207/20132; G06T 9/00; A61C 9/004; H04N 19/176; H04N 19/625; H04N 19/91; H04N 19/85; H03M 7/30
See application file for complete search history.

(56) References Cited

U.S. PATENT DOCUMENTS

| | | | |
|---|---|---|---|
| 6,227,851 | B1 | 5/2001 | Chishti et al. |
| 6,299,440 | B1 | 10/2001 | Phan et al. |
| 6,318,994 | B1 | 11/2001 | Chishti et al. |
| 6,371,761 | B1 | 4/2002 | Cheang et al. |
| 6,386,878 | B1 | 5/2002 | Pavlovskaia et al. |
| 6,406,292 | B1 | 6/2002 | Chishti et al. |
| 6,409,504 | B1 | 6/2002 | Jones et al. |
| 6,457,972 | B1 | 10/2002 | Chishti et al. |
| 6,463,344 | B1 * | 10/2002 | Pavloskaia ............. G16H 50/50 700/118 |
| 6,488,499 | B1 | 12/2002 | Miller |
| 6,514,074 | B1 | 2/2003 | Chishti et al. |
| 6,554,611 | B2 | 4/2003 | Chishti et al. |
| 6,582,229 | B1 | 6/2003 | Miller et al. |
| 6,602,070 | B2 | 8/2003 | Miller et al. |
| 6,621,491 | B1 | 9/2003 | Baumrind et al. |
| 6,688,886 | B2 | 2/2004 | Hughes et al. |
| 6,726,478 | B1 | 4/2004 | Isiderio et al. |
| 6,729,876 | B2 | 5/2004 | Chishti et al. |
| 6,739,869 | B1 | 5/2004 | Taub et al. |
| 6,767,208 | B2 | 7/2004 | Kaza |
| 6,783,360 | B2 | 8/2004 | Chishti |
| 7,040,896 | B2 | 5/2006 | Pavlovskaia et al. |
| 7,063,532 | B1 | 6/2006 | Jones et al. |
| 7,074,038 | B1 | 7/2006 | Miller |
| 7,074,039 | B2 | 7/2006 | Kopelman et al. |
| 7,077,647 | B2 | 7/2006 | Choi et al. |
| 7,108,508 | B2 | 9/2006 | Hedge et al. |
| 7,134,874 | B2 | 11/2006 | Chishti et al. |
| 7,156,661 | B2 | 1/2007 | Choi et al. |
| 7,160,107 | B2 | 1/2007 | Kopelman et al. |
| 7,241,142 | B2 | 7/2007 | Abolfathi et al. |
| 7,293,988 | B2 | 11/2007 | Wen |
| 7,309,230 | B2 | 12/2007 | Wen |
| 7,357,634 | B2 | 4/2008 | Knopp |
| 7,555,403 | B2 | 6/2009 | Kopelman et al. |
| 7,637,740 | B2 | 12/2009 | Knopp |
| 7,656,418 | B2 * | 2/2010 | Watkins ................. G06T 19/00 345/620 |
| 7,689,398 | B2 | 3/2010 | Cheng et al. |
| 7,736,147 | B2 | 6/2010 | Kaza et al. |
| 7,746,339 | B2 | 6/2010 | Matov et al. |
| 7,844,356 | B2 | 11/2010 | Matov et al. |
| 7,844,429 | B2 | 11/2010 | Matov et al. |
| 7,865,259 | B2 | 1/2011 | Kuo et al. |
| 7,878,804 | B2 | 2/2011 | Korytov et al. |
| 7,880,751 | B2 | 2/2011 | Kuo et al. |
| 7,904,308 | B2 | 3/2011 | Arnone et al. |
| 7,930,189 | B2 | 4/2011 | Kuo |
| 7,942,672 | B2 | 5/2011 | Kuo |
| 7,970,627 | B2 | 6/2011 | Kuo et al. |
| 7,970,628 | B2 | 6/2011 | Kuo et al. |
| 8,038,444 | B2 | 10/2011 | Kitching et al. |
| 8,044,954 | B2 | 10/2011 | Kitching et al. |
| 8,075,306 | B2 | 12/2011 | Kitching et al. |
| 8,092,215 | B2 | 1/2012 | Stone-Collonge et al. |
| 8,099,268 | B2 | 1/2012 | Kitching et al. |
| 8,108,189 | B2 | 1/2012 | Chelnokov et al. |
| 8,126,726 | B2 | 2/2012 | Matov et al. |
| 8,260,591 | B2 | 9/2012 | Kass et al. |
| 8,275,180 | B2 | 9/2012 | Kuo |
| 8,401,826 | B2 | 3/2013 | Cheng et al. |
| 8,439,672 | B2 | 5/2013 | Matov et al. |
| 8,562,338 | B2 | 10/2013 | Kitching et al. |
| 8,591,225 | B2 | 11/2013 | Wu et al. |
| 8,788,285 | B2 | 7/2014 | Kuo |
| 8,843,381 | B2 | 9/2014 | Kuo et al. |
| 8,874,452 | B2 | 10/2014 | Kuo |
| 8,896,592 | B2 | 11/2014 | Boltunov et al. |
| 8,930,219 | B2 | 1/2015 | Trosien et al. |
| 9,037,439 | B2 | 5/2015 | Kuo et al. |
| 9,060,829 | B2 | 6/2015 | Sterental et al. |
| 9,125,709 | B2 | 9/2015 | Matty |
| 9,211,166 | B2 | 12/2015 | Kuo et al. |
| 9,220,580 | B2 | 12/2015 | Borovinskih et al. |
| 9,364,296 | B2 | 6/2016 | Kuo |
| 9,375,300 | B2 | 6/2016 | Matov et al. |
| 9,414,897 | B2 | 8/2016 | Wu et al. |
| 9,492,245 | B2 | 11/2016 | Sherwood et al. |
| 9,642,678 | B2 | 5/2017 | Kuo |
| 10,248,883 | B2 | 4/2019 | Borovinskih et al. |
| 10,342,638 | B2 | 7/2019 | Kitching et al. |
| 10,463,452 | B2 | 11/2019 | Matov et al. |
| 10,507,087 | B2 * | 12/2019 | Elbaz ................. A61B 1/00016 |
| 10,595,966 | B2 | 3/2020 | Carrier, Jr. et al. |
| 10,617,489 | B2 | 4/2020 | Grove et al. |
| 10,722,328 | B2 | 7/2020 | Velazquez et al. |
| 10,758,322 | B2 | 9/2020 | Pokotilov et al. |
| 10,779,718 | B2 | 9/2020 | Meyer et al. |
| 10,792,127 | B2 | 10/2020 | Kopelman et al. |
| 10,828,130 | B2 | 11/2020 | Pokotilov et al. |
| 10,835,349 | B2 | 11/2020 | Cramer et al. |
| 10,973,611 | B2 | 4/2021 | Pokotilov et al. |
| 10,996,813 | B2 | 5/2021 | Makarenkova et al. |
| 10,997,727 | B2 | 5/2021 | Xue et al. |
| 11,020,205 | B2 | 6/2021 | Li et al. |
| 11,020,206 | B2 | 6/2021 | Shi et al. |
| 11,026,766 | B2 | 6/2021 | Chekh et al. |
| 11,033,359 | B2 | 6/2021 | Velazquez et al. |
| 11,071,608 | B2 | 7/2021 | Derakhshan et al. |
| 11,096,763 | B2 | 8/2021 | Akopov et al. |
| 11,116,605 | B2 | 9/2021 | Nyukhtikov et al. |
| 11,147,652 | B2 | 10/2021 | Mason et al. |
| 11,151,753 | B2 | 10/2021 | Gao et al. |
| 2003/0008259 | A1 | 1/2003 | Kuo et al. |
| 2003/0143509 | A1 | 7/2003 | Kopelman et al. |
| 2003/0207227 | A1 | 11/2003 | Abolfathi |
| 2004/0137400 | A1 | 7/2004 | Chishti et al. |
| 2004/0152036 | A1 | 8/2004 | Abolfathi |
| 2004/0197728 | A1 | 10/2004 | Abolfathi et al. |
| 2004/0259049 | A1 | 12/2004 | Kopelman et al. |
| 2005/0031214 | A1 * | 2/2005 | Zhang .................. H04N 19/597 382/284 |
| 2005/0182654 | A1 | 8/2005 | Abolfathi et al. |
| 2005/0244791 | A1 | 11/2005 | Davis et al. |
| 2006/0127836 | A1 | 6/2006 | Wen |
| 2006/0127852 | A1 | 6/2006 | Wen |
| 2006/0127854 | A1 | 6/2006 | Wen |
| 2006/0275731 | A1 | 12/2006 | Wen et al. |
| 2006/0275736 | A1 | 12/2006 | Wen et al. |
| 2008/0219567 | A1 * | 9/2008 | Claus .................. H04N 19/593 382/232 |

(56) References Cited

U.S. PATENT DOCUMENTS

| | | |
|---|---|---|
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |
| 2016/0242870 A1 | 8/2016 | Matov et al. |
| 2016/0310235 A1 | 10/2016 | Derakhshan et al. |
| 2017/0273760 A1 | 9/2017 | Morton et al. |
| 2017/0310968 A1 | 10/2017 | Rossato et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0074712 A1* | 3/2020 | Wu .................... G06V 10/25 |
| 2020/0085546 A1 | 3/2020 | Li et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0049461 A1* | 2/2021 | Takeshima ............ G16H 30/40 |
| 2021/0073998 A1 | 3/2021 | Brown et al. |
| 2021/0134436 A1 | 5/2021 | Meyer et al. |
| 2021/0174477 A1 | 6/2021 | Shi et al. |

OTHER PUBLICATIONS

Santos, Joao M., et al. "Compression of medical images using MRP with bi-directional prediction and histogram packing." 2016 Picture Coding Symposium (PCS). IEEE, Dec. 2016.*

Srivastava, Meenakshi, and Suneeta Agarwal. "Compression of medical images using their symmetry." 2018 5th IEEE Uttar Pradesh section international conference on electrical, electronics and computer engineering (UPCON). IEEE, 2018. (Year: 2018).*

Santos, Joao M., et al. "Compression of medical images using MRP with bi-directional prediction and histogram packing." 2016 Picture Coding Symposium (PCS). IEEE, 2016. (Year: 2016).*

Philips W., et al., "State-of-the-art Techniques For Lossless Compression of 3D Medical Image Sets", Computerized Medical Imaging and Graphics, Pergamon Press, Jan. 1, 2001, vol. 25, pp. 173-185, XP007916939.

Santos J.M., et al., "Compression of Medical Images Using MRP With Bi-directional Prediction And Histogram Packing", 2016 Picture Coding Symposium (PCS), IEEE, Dec. 4, 2016, pp. 1-5, XP033086941.

Srivastava M., et al., "Compression of Medical Images using their Symmetry", 2018 5th IEEE Uttar Pradesh Section International Conference on Electrical, Electronics and Computer Engineering (UPCON), IEEE, Nov. 2, 2018, pp. 1-5, XP033489467.

Udupa J., et al., "Three-Dimensional Visualization: Principles and Approaches" In: "Handbook of Medical Imaging—vol. 3: Display and PACS", Oct. 3, 2000, XP055805419.

Chiang et al.; Demonstration of the mpeg-2, mpeg-4 and h. 263 video coding standards; In Proceedings of First Signal Processing Society Workshop on Multimedia Signal Processing; IEEE; pp. 576-580; Jun. 23, 1997.

* cited by examiner

1100

Uncompressed (white) vs compressed @ compression x5 (red)

1102

Uncompressed (white) vs compressed @ compression x1986 (red)

MEDICAL IMAGING DATA COMPRESSION AND EXTRACTION ON CLIENT SIDE

CLAIM OF PRIORITY

This patent application claims priority to U.S. Provisional Patent Application No. 62/979,325, filed on Feb. 20, 2020, titled "MEDICAL IMAGING DATA COMPRESSION AND EXTRACTION ON CLIENT SIDE," herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND

Modern medicine increasingly relies on medical imaging for diagnosing and treating patients. For example, medical imaging may provide visual representations of the interior of a patient's body. Various medical imaging techniques, such as X-ray radiography, CT-scan imaging, magnetic resonance imaging (MRI), and ultrasonography, can be used to produce image data of a patient's body. For example, cone beam computed tomography (CBCT) is one such medical imaging technique in which X-rays form a cone for scanning that is used to image the patient. During the imaging, the CBCT scanner may be rotated around a region of interest to obtain numerous (e.g., hundreds or thousands) of distinct images forming a volumetric data set. The volumetric data may be used to reconstruct a digital volume of the region of interest. The digital volume may be defined by three-dimensional voxels of anatomical data.

However, as medical imaging techniques become more sophisticated, the amount of image data has increased and the prior approaches to handling data can be less than ideal in at least some respects. The above imaging approaches may be used for dental or orthodontic imaging, and in at least some instances the treatment professional can be located remotely from the imaging system. Although a dental or orthodontic practitioner may be able to view and manipulate the digital volume to diagnose and treat the region of interest, there can be significant delays in transmitting data in at least some instances. Also, with some approaches such as teeth segmentation for the planning of dental and orthodontic procedures, the dataset can be transferred to a remote location for processing the volumetric data. Although the digital volume may provide an accurate 3D representation, the volumetric data storage and transfer requirements may burdensome and less than ideal in at least some instances. For example, the CBCT scanner may generate volumetric data, and a large amount of volumetric data may be difficult and time consuming to consistently transfer to a remote location. Also, it may be more difficult than ideal to store or otherwise archive multiple sets of volumetric data in multiple locations, for example.

The present disclosure, therefore, identifies and addresses a need for systems and method for client-side compression and extraction of medical imaging data.

SUMMARY OF THE DISCLOSURE

Described herein are methods and apparatuses (e.g., systems and devices, including software, hardware and firmware) for compression and extraction of imaging data. In particular, these methods and apparatuses may be used for medical imaging data, such as three-dimensional (3D) volumetric image data from, for instance (but not limited to), a CBCT scanner. In general, the 3D volumetric image data may be static data. The 3D volumetric image data may include a plurality of 2D images (sections or slices) through which may collectively be referred to as a 3D volume. The 3D volume may include predefined section or images (2D image), or these 2D section so images may be generated from the 3D volume.

This 3D volumetric image data may be pre-processed by aligning it, for example, by analyzing a relevant region of the 3D volumetric data. Pre-processing may also include selecting and/or setting coordinate axes (e.g., x, y, z). The coordinate axes may be based on one or more identified anatomical planes, identified from the image data. Pre-processing may therefore be used to align and maximize the symmetry within the 3D volumetric image data. In some examples, pre-processing may include cropping the 3D volume, e.g., parallel to the anatomical planes identified, so that 3D volume has a regular (e.g., rectangular, cubic, etc.) shape. In some examples the 3D volume may be padded, such as with blank space, to maintain the regular shape. The 3D volumetric image data may also be preprocessed by reducing the dynamic range and/or by segmenting to identify predetermined clinically relevant features. For dental imaging in particular, the clinically relevant features may include bone, soft tissue (e.g., gums, gingiva, etc.), tooth roots, tooth crown, tooth internal structures (e.g., dentin, enamel, etc.), and the like.

The pre-processed 3D volumetric image data may be compressed using any appropriate compression technique. In particular one or more video compression techniques may be used by converting a spatial axis of the 3D volume of the 3D volumetric image data into a time axis to form a time sequence of 2D images and applying a video compression scheme. By compressing the pre-processed 3D volumetric image data, the methods and apparatuses described herein may provide a client-side solution for compressing and/or extracting medical imaging data. The systems and methods described herein may improve the transmission and storing of medical imaging data, by reducing an amount of data to be uploaded to a server.

In addition, the systems and methods described herein may improve the functioning of a computing device by more efficiently applying a compression scheme and reducing bandwidth by transmitting compressed data. These systems and methods may also improve the field of medical imaging by reducing data storage requirements for computational processes.

Also described herein are apparatuses (e.g., systems) for performing any of the methods described herein. These apparatuses may be integrated with an imaging device or system (such as CBCT scanner, an ultrasound scanner, etc.). For example, described herein are systems for compressing a three-dimensional (3D) volumetric image data set including a plurality of image sections forming a 3D volume, the system comprising: one or more processors; a memory coupled to the one or more processors, the memory storing computer-program instructions, that, when executed by the one or more processors, perform a computer-implemented method comprising: identifying one or more anatomic planes within the 3D volumetric image data set and setting coordinate planes using the one or more anatomic planes; cropping the 3D volume parallel to the coordinate planes; adjusting the dynamic range of the 3D volumetric image data set; and converting a spatial axis of the 3D volume into a time axis to form a time sequence of 2D images and applying a video compression scheme to the time sequence of 2D images to form a compressed 3D volumetric image data set.

The computer implemented method may identify the one or more anatomic planes within the 3D volumetric image data set and sets the coordinate planes to increase the symmetry of the coordinate planes. In some examples the computer implemented method crops the 3D volume parallel to the coordinate planes to minimize empty regions of the 3D volume. The computer implemented method may further include padding the 3D volume with empty regions to keep the 3D volume symmetrical after cropping. In some examples the computer implemented method adjusts the dynamic range of the 3D volumetric image data set by histogram analysis. For example, the computer implemented method may adjust the dynamic range of the 3D volumetric image data set by segmenting the 3D volumetric image data set using clinically-relevant regions (e.g., the clinically-relevant regions may comprise: soft tissue, bone, tooth crowns and tooth roots, etc.).

For example, described herein are methods of compressing a three-dimensional (3D) volumetric image data set. The 3D volumetric data set may include a plurality of image sections forming a 3D volume. For example a 3D (e.g., static) volumetric image data set may be compressed by: identifying one or more anatomic planes within the 3D volumetric image data set and setting coordinate planes using the one or more anatomic planes; cropping the 3D volume parallel to the at least two coordinate planes; adjusting the dynamic range of the 3D volumetric image data set; and converting a spatial axis of the 3D volume into a time axis to form a time sequence of 2D images and applying a video compression scheme to the time sequence of 2D images to form a compressed 3D volumetric image data set.

Any of these methods may include identifying the one or more anatomic planes within the 3D volumetric image data set and settings the coordinate planes by setting the coordinate planes to increase the symmetry of the coordinate planes. In some examples the method also includes cropping the 3D volume parallel to the coordinate planes to minimize empty regions of the 3D volume, and/or padding the 3D volume with empty regions to keep the 3D volume symmetrical after cropping.

Adjusting dynamic range of the 3D volumetric image data set may include adjusting by histogram analysis. Any of these methods may include segmenting the 3D volumetric image data set using clinically-relevant regions. The clinically-relevant regions may include, for example: soft tissue, bone, tooth crowns and tooth roots.

Any of these methods may include dividing the image sections forming the 3D volume into a first half that is symmetric with a second half, determining differences between the first half and the second half, and reducing the 3D volume by replacing the second half with differences between first half and the second half before converting the spatial axis of the 3D volume into the time axis.

These methods may also include storing or transmitting the compressed 3D volumetric image data set. For example, any of these methods may include transmitting the compressed 3D volumetric data set to a remote server and decompressing the 3D volumetric data set on the remote server. The remote server may decompress the 3D volumetric image data set.

In any of these methods applying the video compression scheme to the time sequence of 2D images to form the compressed 3D volumetric image data set may comprise forming the compressed 3D volumetric image data set at a compression rate of between 50 and 2500 times. In some examples, applying the video compression scheme to the time sequence of 2D images to form the compressed 3D volumetric image data set comprises forming the compressed 3D volumetric image data set at a compression rate of 50 times or more. In general, these methods may include compressing with a Dice coefficient of greater than 0.90.

In any of these methods, applying the video compression scheme to the time sequence of 2D images may comprise applying macroblock compression using a discrete cosine transformation (DCT). Any of these methods may include encoding the compressed 3D volumetric image data set using entropy encoding.

For example, a method of compressing a three-dimensional (3D) volumetric image data set including a plurality of image sections forming a 3D volume, may include: identifying at least two anatomic planes within the 3D volumetric image data set and setting at least two coordinate planes using the at least two anatomic planes to increase the symmetry of the coordinate planes; cropping the 3D volume parallel to the coordinate planes; adjusting the dynamic [rage] range of the 3D volumetric image data set by histogram analysis and segmenting the 3D volumetric image data set using clinically-relevant regions comprising: soft tissue, bone, tooth crowns and tooth roots; dividing the image sections forming the 3D volume into a first half that is symmetric with a second half, determining differences between the first half and the second half and reducing the 3D volume by replacing the second half with differences between first half and the second half; applying a video compression scheme to the 3D volume to form a compressed 3D volumetric image data set by converting a spatial axis of the 3D volume into a time axis to form a time sequence of 2D images; and storing or transmitting the compressed 3D volumetric image data set.

Any of these computer implemented methods may further comprise dividing the image sections forming the 3D volume into a first half that is symmetric with a second half, determining differences between the first half and the second half and reducing the 3D volume by replacing the second half with differences between first half and the second half before converting the spatial axis of the 3D volume into the time axis.

As mentioned, any of these systems may include an imaging device in communication with the one or more processors (e.g., CBCT system, etc.).

The computer implemented method may further comprises storing or transmitting the compressed 3D volumetric image data set. In some examples the computer implemented method further comprises transmitting the compressed 3D volumetric data set to a remote server and decompressing the 3D volumetric image data set on the remote server. The computer implemented method may apply the video compression scheme to the time sequence of 2D images to form the compressed 3D volumetric image data set at a compression rate of between 50 and 2500 times. In some examples the computer implemented method applies the video compression scheme to the time sequence of 2D images to form the compressed 3D volumetric image data set at a compression rate of 50 times or more. The compression may be done with a Dice score of greater than 0.9.

The computer implemented method may apply the video compression scheme by applying macroblock compression using a discrete cosine transformation (DCT) to the time sequence of 2D images to form a compressed 3D volumetric image data set.

In some examples the computer implemented method further comprises encoding the compressed 3D volumetric image data set using entropy encoding.

For example, a system for compressing a three-dimensional (3D) volumetric image data set including a plurality of image sections forming a 3D volume, the system comprising: one or more processors; a memory coupled to the one or more processors, the memory storing computer-program instructions, that, when executed by the one or more processors, perform a computer-implemented method comprising: identifying at least two anatomic planes within the 3D volumetric image data set and setting at least two coordinate planes using the at least two anatomic planes to increase the symmetry of the coordinate planes; cropping the 3D volume parallel to the coordinate planes; adjusting the dynamic range of the 3D volumetric image data set by histogram analysis and segmenting the 3D volumetric image data set using clinically-relevant regions comprising: soft tissue, bone, tooth crowns and tooth roots; dividing the image sections forming the 3D volume into a first half that is symmetric with a second half, determining differences between the first half and the second half and reducing the 3D volume by replacing the second half with differences between first half and the second half; applying a video compression scheme to the 3D volume to form a compressed 3D volumetric image data set by converting a spatial axis of the 3D volume into a time axis to form a time sequence of 2D images; and storing or transmitting the compressed 3D volumetric image data set.

BRIEF DESCRIPTION OF THE DRAWINGS

A better understanding of the features, advantages and principles of the present disclosure will be obtained by reference to the following detailed description that sets forth illustrative embodiments, and the accompanying drawings of which.

DETAILED DESCRIPTION

The following detailed description and provides a better understanding of the features and advantages of the inventions described in the present disclosure in accordance with the examples disclosed herein. Although the detailed description includes many specific examples, these are provided by way of example only and should not be construed as limiting the scope of the inventions disclosed herein.

Figure 1:
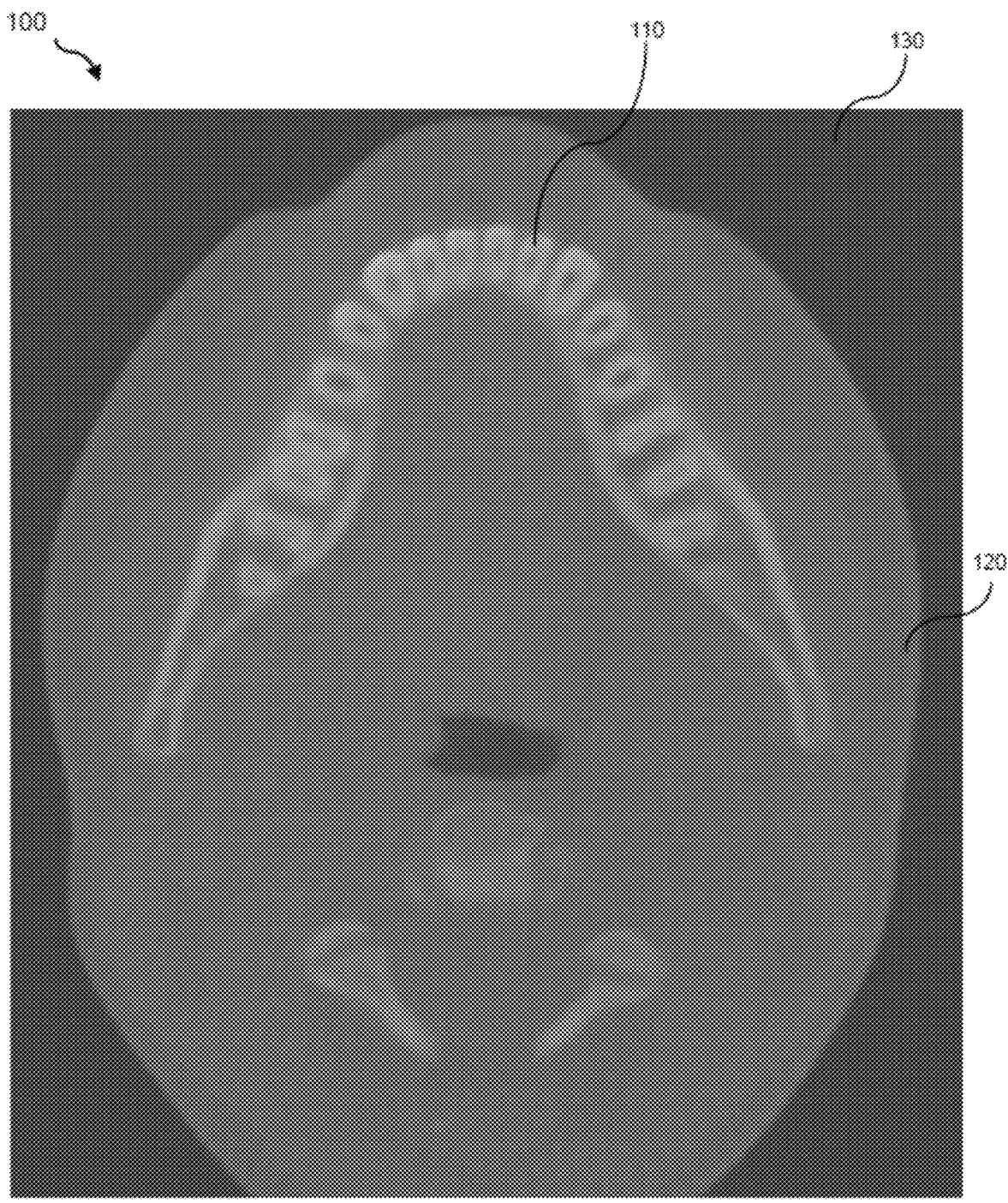
FIG. 1 shows a portion of 3D volumetric image data, in accordance with some examples.
Figure 2:
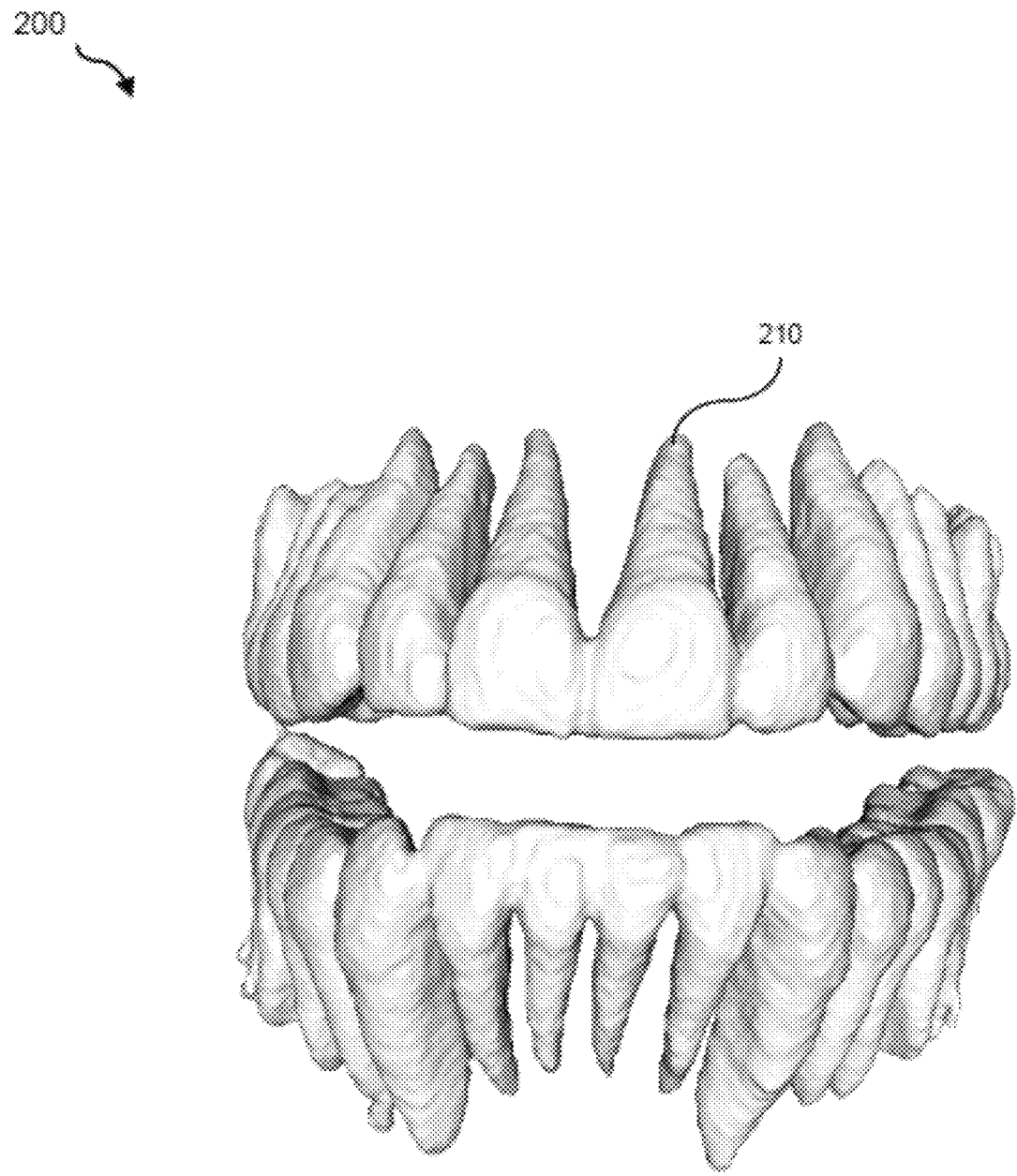
FIG. 2 shows a reconstruction of a patient's teeth based on 3D volumetric image data, in accordance with some examples.

The following will provide, with reference to FIGS. 1-2, detailed descriptions of imaging and modeling. Theses examples may be specific to medical (e.g., dental) systems and methods, but the methods and apparatuses described herein may be generally applied to any (including non-medical) imaging technique. Detailed descriptions of example systems for compressing and extracting medical imaging data will be provided in connection with FIGS. 3-4. Detailed descriptions of corresponding computer-implemented methods will also be provided in connection with FIG. 5. Detailed descriptions of exemplary geometric preprocessing will be provided in connection with FIG. 6. Detailed descriptions of histogram analysis will be provided in connection with FIG. 7. Detailed descriptions of voxel reencoding will be provided in connection with FIG. 8. Detailed descriptions of computer-implemented methods for extracting medical imaging data will be provided in connection with FIG. 9. Detailed descriptions of evaluating compression results will also be provided in connection with FIG. 10 and FIG. 11. Detailed descriptions of additional methods will also be provided in connection with FIG. 12. In addition, detailed descriptions of an example computing system and network architecture capable of implementing one or more of the examples described herein will be provided in connection with FIGS. 13 and 14, respectively.

FIG. 1 illustrates image data 100, which may be a single image from a 3D volumetric image data such as CBCT scan data. The 3D volumetric image data may include a plurality of separate images taken around a subject. Each image may correspond to, for example, a scan of the subject taken at a different angle, a different scanning offset, etc. The 3D volumetric data may be used to reconstruct a digital volume of the subject. The digital volume may comprise voxels which represent values in the three-dimensional space. The values may correspond to anatomical structures. As seen in FIG. 1, image data 100 includes a bone structure 110, a tissue structure 120, and an empty space 130.

FIG. 2 illustrates a reconstruction 200 having various tooth structures 210. 3D volumetric data may be reconstructed into a 3D model of the subject. In some examples, segmentation may be performed on the 3D volumetric data to remove non-relevant regions from the 3D model. Reconstruction 200 includes only tooth structures 210 without non-relevant regions. Orthodontic practitioners may often utilize reconstructions such as reconstruction 200 to diagnose a patient's teeth. Thus, accuracy of reconstruction 200 may be an important consideration. Although a larger 3D volumetric image data set may produce higher resolution reconstructions, the data storage requirements may be prohibitive.

Figure 3:
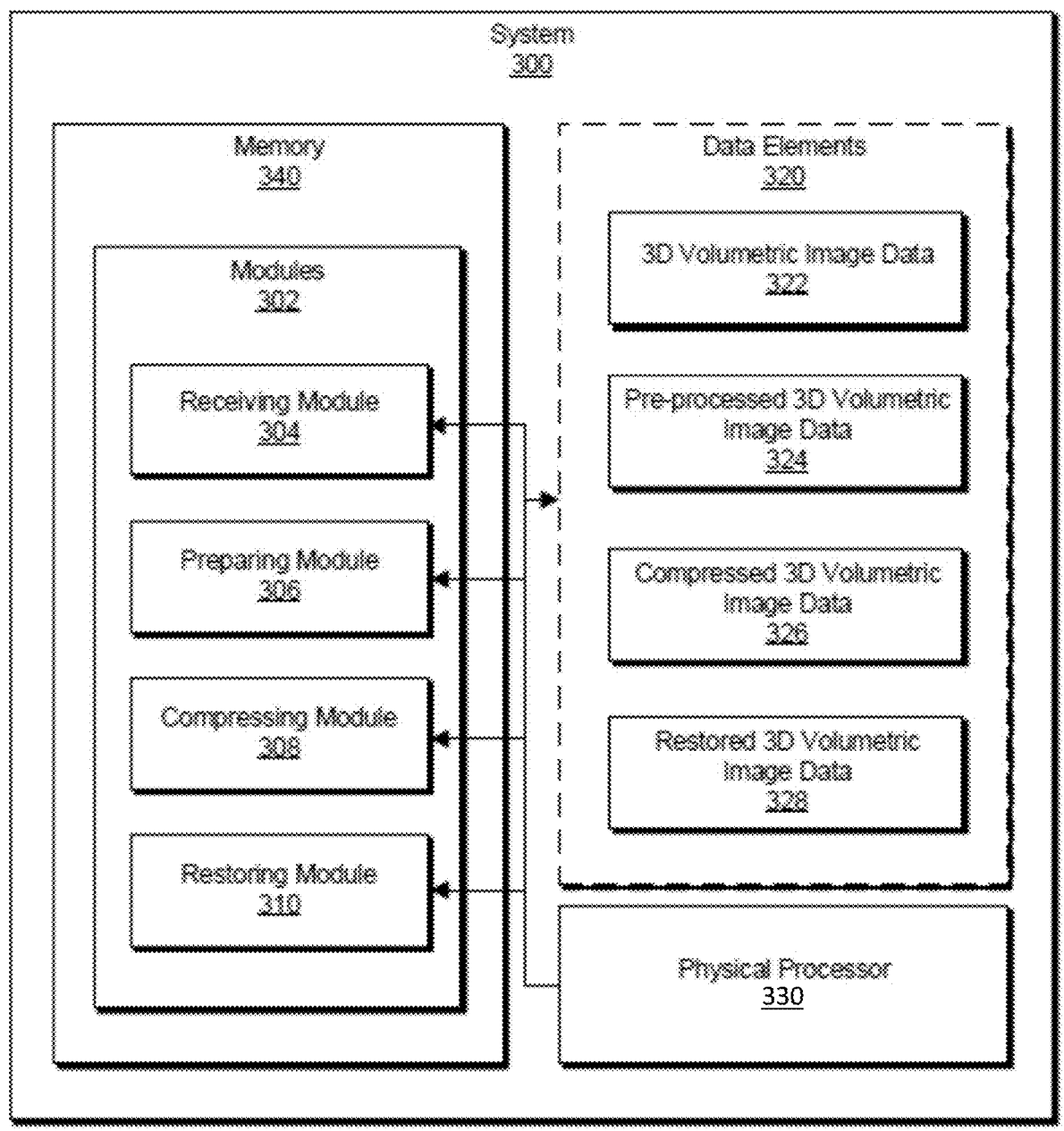
FIG. 3 shows a block diagram of an example system for medical imaging data compression and extraction, in accordance with some examples.

FIG. 3 is a block diagram of an example system 300 for compressing and extracting medical imaging data. As illustrated in this figure, example system 300 may include one or more modules 302 for performing one or more tasks. As will be explained in greater detail below, modules 302 may include a receiving module 304, a preparing module 306, a compressing module 308, and a restoring module 310. Although illustrated as separate elements, one or more of modules 302 in FIG. 3 may represent portions of a single module or application.

In certain examples, one or more of modules 302 in FIG. 3 may represent one or more software applications or programs that, when executed by a computing device, may cause the computing device to perform one or more tasks. For example, and as will be described in greater detail below, one or more of modules 302 may represent modules stored and configured to run on one or more computing devices, such as the devices illustrated in FIG. 4 (e.g., computing device 402 and/or server 406). One or more of modules 302 in FIG. 3 may also represent all or portions of one or more special-purpose computers configured to perform one or more tasks.

As illustrated in FIG. 3, example system 300 may also include one or more memory devices, such as memory 340. Memory 340 generally represents any type or form of volatile or non-volatile storage device or medium capable of storing data and/or computer-readable instructions. In one example, memory 340 may store, load, and/or maintain one or more of modules 302. Examples of memory 340 include, without limitation, Random Access Memory (RAM), Read Only Memory (ROM), flash memory, Hard Disk Drives (HDDs), Solid-State Drives (SSDs), optical disk drives, caches, variations or combinations of one or more of the same, and/or any other suitable storage memory.

As illustrated in FIG. 3, example system 300 may also include one or more physical processors, such as physical processor 330. Physical processor 330 generally represents any type or form of hardware-implemented processing unit capable of interpreting and/or executing computer-readable instructions. In one example, physical processor 330 may access and/or modify one or more of modules 302 stored in memory 340. Additionally or alternatively, physical processor 330 may execute one or more of modules 302 to facilitate compression and/or extraction of medical imaging data. Examples of physical processor 330 include, without limitation, microprocessors, microcontrollers, Central Processing Units (CPUs), Graphics Processing Units (GPUs) Field-Programmable Gate Arrays (FPGAs) that implement softcore processors, Application-Specific Integrated Circuits (ASICs), portions of one or more of the same, variations or combinations of one or more of the same, and/or any other suitable physical processor.

As illustrated in FIG. 3, example system 300 may also include one or more data elements 320, such as 3D volumetric image data 322, pre-processed 3D volumetric image data 324, compressed 3D volumetric image data 326, and restored 3D volumetric image data 328. Data elements 320 generally represent any type or form of data, such as medical imaging data and permutations thereof, as will be described further below.

Figure 4:
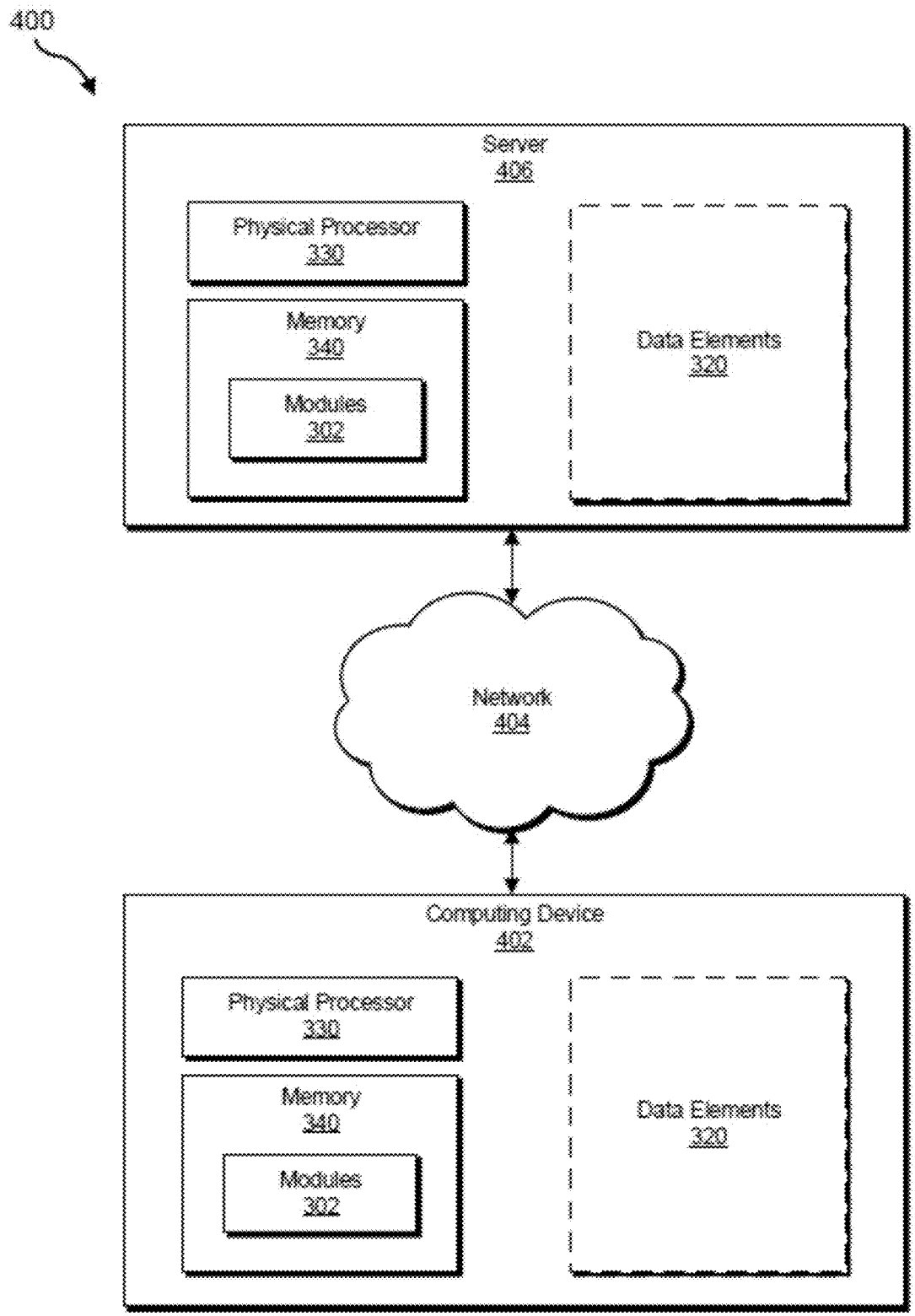
FIG. 4 shows a block diagram of an additional example system for compression and extraction of medical imaging data, in accordance with some examples.

Example system 300 in FIG. 3 may be implemented in a variety of ways. For example, all or a portion of example system 300 may represent portions of example system 400 in FIG. 4. As shown in FIG. 4, system 400 may include a computing device 402 in communication with a server 406 via a network 404. In one example, all or a portion of the functionality of modules 302 may be performed by computing device 402, server 406, and/or any other suitable computing system. As will be described in greater detail below, one or more of modules 302 from FIG. 3 may, when executed by at least one processor of computing device 402 and/or server 406, enable computing device 402 and/or server 406 to compress and/or extract medical imaging data. For example, and as will be described in greater detail below, one or more of modules 302 may cause computing device 402 and/or server 406 to prepare pre-processed 3D volumetric image data and compress the pre-processed 3D volumetric image data into compressed 3D volumetric image data.

Computing device 402 generally represents any type or form of computing device capable of reading computer-executable instructions. Computing device 402 may be a user device, such as a desktop computer or mobile device. Additional examples of computing device 402 include, without limitation, laptops, tablets, desktops, servers, cellular phones, Personal Digital Assistants (PDAs), multimedia players, embedded systems, wearable devices (e.g., smart watches, smart glasses, etc.), smart vehicles, smart packaging (e.g., active or intelligent packaging), gaming consoles, so-called Internet-of-Things devices (e.g., smart appliances, etc.), variations or combinations of one or more of the same, and/or any other suitable computing device.

Server 406 generally represents any type or form of computing device that is capable of storing and/or processing imaging data. Additional examples of server 406 include, without limitation, security servers, application servers, web servers, storage servers, and/or database servers configured to run certain software applications and/or provide various security, web, storage, and/or database services. Although illustrated as a single entity in FIG. 4, server 406 may include and/or represent a plurality of servers that work and/or operate in conjunction with one another.

Network 404 generally represents any medium or architecture capable of facilitating communication or data transfer. In one example, network 404 may facilitate communication between computing device 402 and server 406. In this example, network 404 may facilitate communication or data transfer using wireless and/or wired connections. Examples of network 404 include, without limitation, an intranet, a Wide Area Network (WAN), a Local Area Network (LAN), a Personal Area Network (PAN), the Internet, Power Line Communications (PLC), a cellular network (e.g., a Global System for Mobile Communications (GSM) network), portions of one or more of the same, variations or combinations of one or more of the same, and/or any other suitable network.

Figure 5:
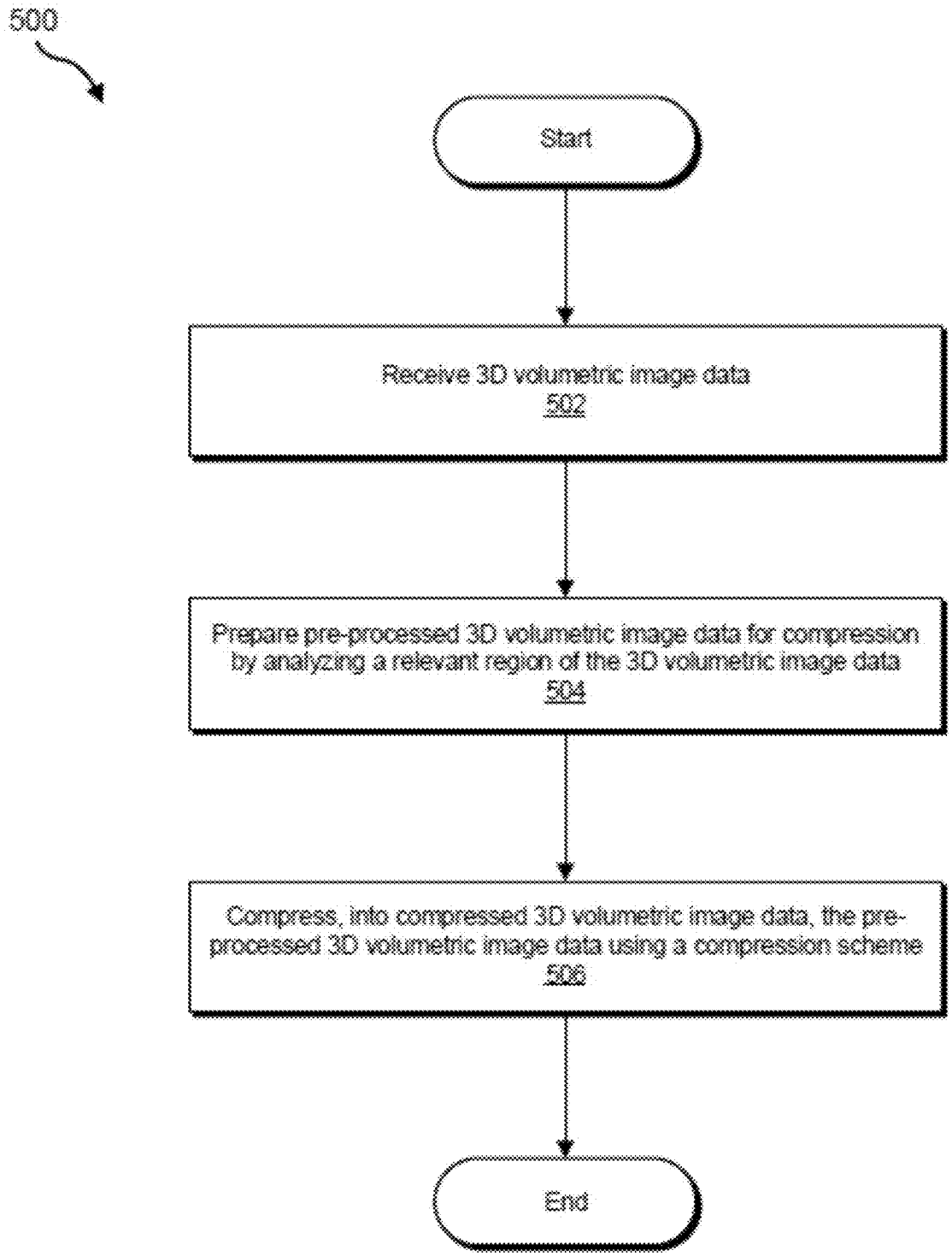
FIG. 5 shows a flow diagram of an example method for compression of medical imaging data, in accordance with some examples.

FIG. 5 is a flow diagram of an example computer-implemented method 500 for compressing medical imaging data. The steps shown in FIG. 5 may be performed by any suitable computer-executable code and/or computing system, including system 300 in FIG. 3, system 400 in FIG. 4, and/or variations or combinations of one or more of the same. In one example, each of the steps shown in FIG. 5 may represent an algorithm whose structure includes and/or is represented by multiple sub-steps, examples of which will be provided in greater detail below.

As illustrated in FIG. 5, at step 502 one or more of the systems described herein may receive the 3D volumetric image data. For example, receiving module 304, as part of computing device 402, may receive 3D volumetric image data 322. 3D volumetric image data 322 may comprise scan data of a patient. 3D volumetric image data 322 may include a computed tomography (CT) image, a cone beam computed tomography image (CBCT), or a magnetic resonance imaging (MRI) image. 3D volumetric image data 322 may include a 3D volumetric digital imaging and communications in medicine (DICOM) image.

In one example, an orthodontic practitioner may receive raw CBCT scan data of a patient's head from a scanner onto his computing device. For example, 3D volumetric image data 322 may include a plurality of teeth.

In other examples, 3D volumetric image data 322 may include one or more segmentable tissue structures. Each of the one or more segmentable tissue structures may include an outer surface enclosing an interior of the one or more segmentable tissue structures. More specifically, the one or more segmentable tissue structures may include a plurality of teeth. Each of the plurality of teeth may include an outer surface enclosing an interior.

As illustrated in FIG. 5, at step 504 one or more of the systems described herein may prepared pre-processed 3D volumetric image data for compression by analyzing a relevant region of the 3D volumetric image data. For example, preparing module 306, as part of computing device 402, may prepare pre-processed 3D volumetric image data 324 by analyzing a relevant region of 3D volumetric image data 322. Pre-processed 3D volumetric image data 324 may include data that preparing module 306 has analyzed to determine refinements and other modifications to optimize compression. Preparing module 306 may prepare pre-processed 3D volumetric image data 324 in various ways.

In some examples, preparing module 306 may prepare pre-processed 3D volumetric image data 324 by performing geometric preprocessing on 3D volumetric image data 322. For instance, preparing module 306 may identify an anatomical plane from 3D volumetric image data 322. The anatomical plane may be one or more of a sagittal plane, a coronal plane, or an axial plane. Preparing module 306 may rotate a volume captured in 3D volumetric image data 322 to align the anatomical plane to a coordinate axis, which may be defined in 3D volumetric image data 322. Pre-processed 3D volumetric image data 324 may include the rotated volume.

Figure 6B:
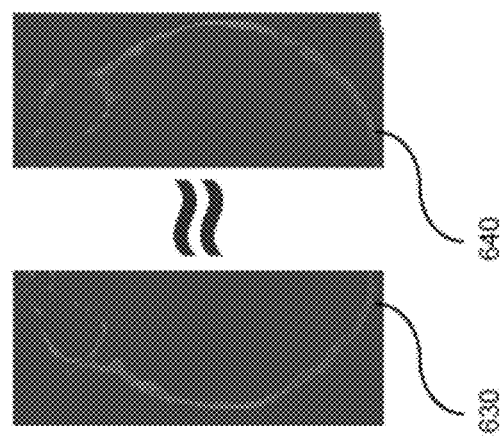
FIGS. 6A and 6B show diagrams of geometric preprocessing, in accordance with some examples.
Figure 6A:
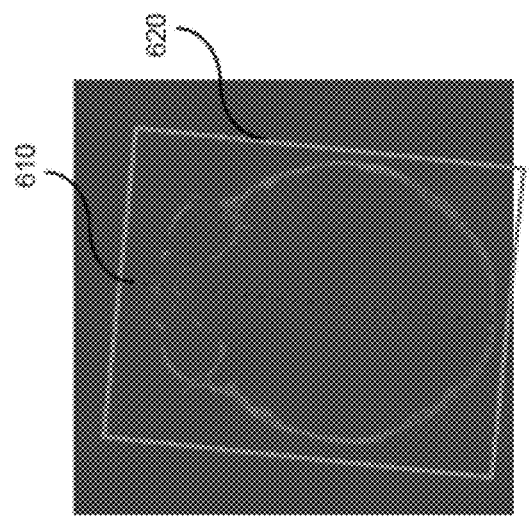

FIG. 6A illustrates image 600 including an anatomical plane 610 and a volume 620. As seen in FIG. 6A, volume 620 may be rotated to align anatomical plane 610 with a coordinate axis. For example, volume 620 may be rotated to make anatomical plane 610 parallel with an X, Y, or Z axis. Such rotation may reduce a complexity of a data structure (e.g., by making more symmetrical) for pre-processed 3D volumetric image data 324 which may further optimize compression.

Preparing module 306 may perform geometric preprocessing by identifying an axis of symmetry from 3D volumetric image data 322 to divide a volume captured in 3D volumetric image data 322 into a first part and a second part. Preparing module 306 may determine a difference between the first part and the second part and store, as pre-processed 3D volumetric image data 324, the first part and the difference.

FIG. 6B illustrates a segmented image 602 including a first part 630 and a second part 640. First part 630 and second part 640 may be divided from an axis of symmetry (e.g. anatomical plane 610 in FIG. 6A) such that first part 630 may be nearly symmetrical with second part 640. Although first part 630 may resemble a mirror image of second part 640, difference may exist which may include relevant data. However, storing first part 630 and the difference may reduce a storage size of pre-processed 3D volumetric image data 324 compared to that of 3D volumetric image data 322 and may further optimize compression.

Preparing module 306 may also perform geometric preprocessing by identifying a non-relevant region from 3D volumetric image data 322, and cropping the non-relevant region such that pre-processed 3D volumetric image data 324 may not include the non-relevant region. The non-relevant region may be an empty region. For example, portions of empty space 130 in FIG. 1 may be cropped. Cropping non-relevant regions may reduce a storage size of pre-processed 3D volumetric image data 324 compared to that of 3D volumetric image data 322 and may further optimize compression.

In some examples, preparing module 306 may prepare pre-processed 3D volumetric image data 324 by identifying a root structure or a bone structure from 3D volumetric image data 322 as the relevant region and marking the identified relevant region. For example, preparing module 306 may identify and mark bone structure 110 in FIG. 1. Preparing module 306 may perform segmentation to segment the volume into relevant and non-relevant regions.

Figure 7:
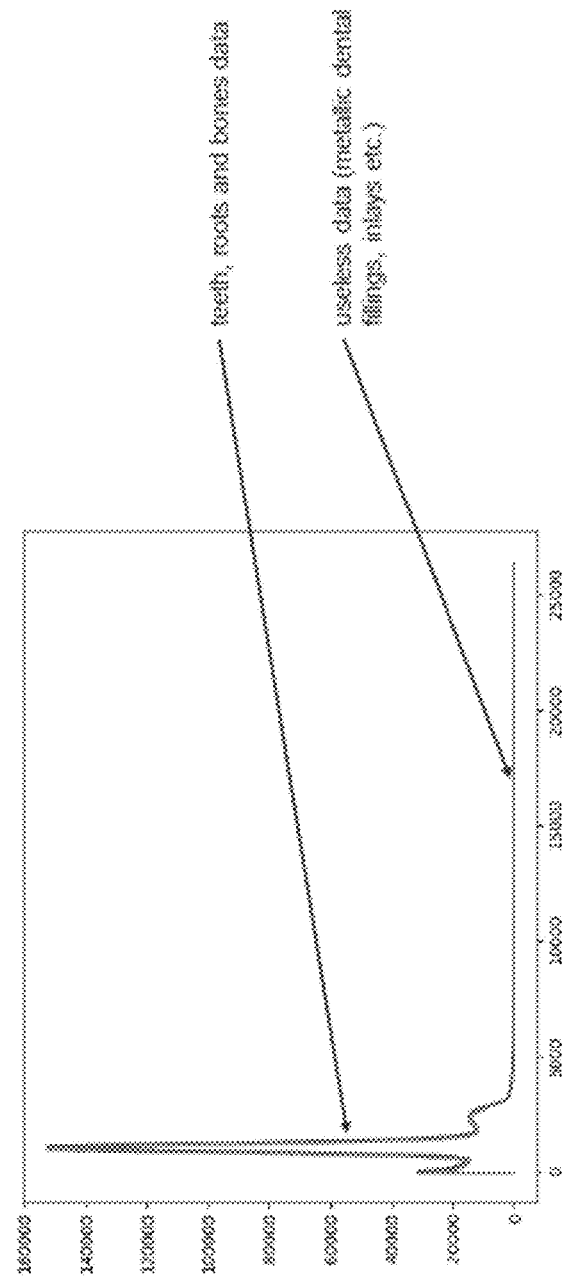
FIG. 7 shows an exemplary graph of histogram analysis, in accordance with some examples.

In some examples, preparing module 306 may perform a histogram analysis to identify the relevant region. FIG. 7 illustrates a histogram graph 700. As seen in FIG. 7, certain values may correspond to certain types of structures. Preparing module 306 may analyze the values of the voxels of 3D volumetric image data 322.

Marking the relevant regions may facilitate further preprocessing of 3D volumetric image data 322. In some examples, preparing module 306 may reencode voxels of 3D volumetric image data 322 to decrease a dynamic range of bits per voxel. Each voxel may include a value corresponding to a type of anatomical structure. As a number of types increases (e.g., a range of possible values increases), a number of bits required for storing each value for each voxel may increase. Increasing the bits per voxel may result in increased data storage requirements for 3D volumetric image data 322. However, because certain types of structures may not be relevant, for example as determined through histogram analysis, less data may be preserved with respect to the non-relevant regions without losing data with respect to relevant regions.

For example, the types of structures may be reduced to empty space, soft tissue, bone, or tooth. With 4 possible intensity values, each voxel may be encoded with 2 bits per voxel. In other examples, a more detailed segmentation may result in 4 to 8 bits per voxel. Thus, the dynamic range may be decreased from greater than 8 bits per voxel to 2 to 8 bits per voxel.

Figure 8:
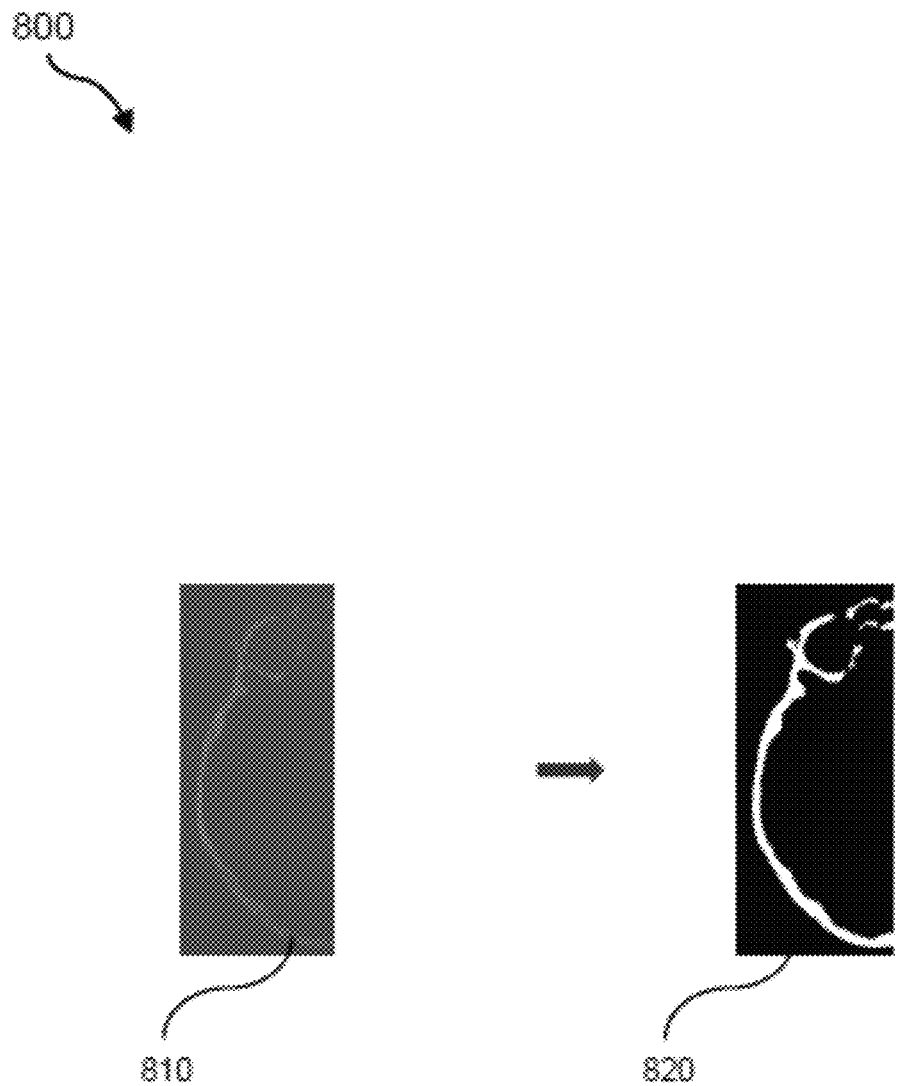
FIG. 8 shows an example of reencoding voxels, in accordance with some examples.

FIG. 8 illustrates a reencoding 800 of image data 810 into reencoded image data 820. As seen in FIG. 8, reencoding may result in some loss of detail while preserving relevant structural details.

Returning to FIG. 5, at step 506 one or more of the systems described herein may compress, into compressed 3D volumetric image data, the pre-processed 3D volumetric image data using a compression scheme. For example, compressing module 308, as part of computing device 402, may compress pre-processed 3D volumetric image data 324 into compressed 3D volumetric image data 326 using a compression scheme. Compressing module 308 may compress pre-processed 3D volumetric image data 324 in various ways.

In some examples, the compression scheme may be a video codec. Because the volumetric image data (e.g., 3D volumetric image data 322 and pre-processed 3D volumetric image data 324) may include a plurality of images, similar to a video file, compressing module 308 may utilize a video codec. The preprocessing performed by preparing module 306 may further optimize pre-processed 3D volumetric image data 324 for compression. In some examples, the compression scheme may include a discrete cosine transformation (DCT). In some examples, the compression scheme may include a motion compensation scheme. In some examples, the compression scheme may include an entropy encoding scheme.

Figure 9:
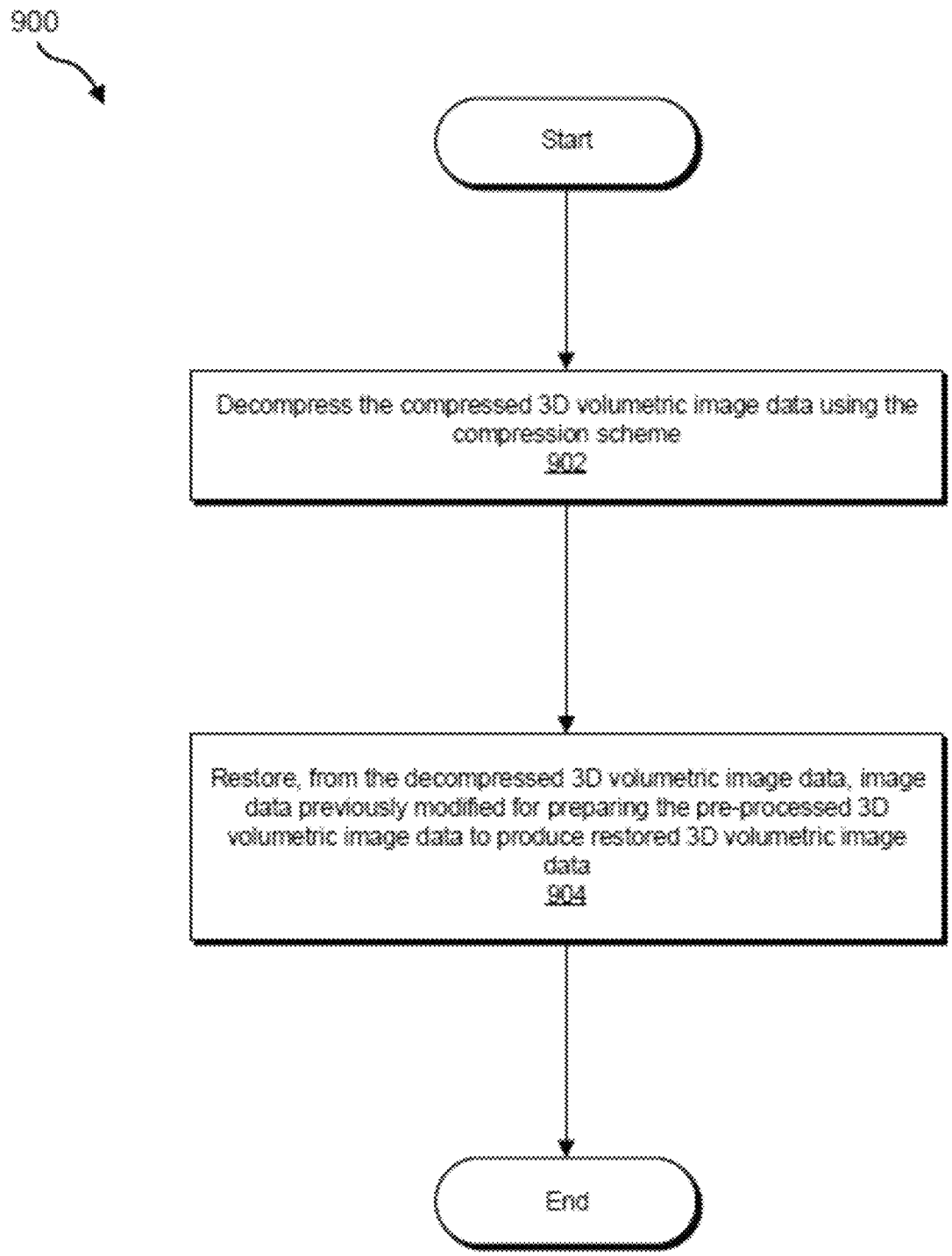
FIG. 9 shows a flow diagram of an example method for extracting medical imaging data from compressed data, in accordance with some examples.

FIG. 9 is a flow diagram of an example computer-implemented method 900 for extracting medical imaging data from compressed data. The steps shown in FIG. 9 may be performed by any suitable computer-executable code and/or computing system, including system 300 in FIG. 3, system 400 in FIG. 4, and/or variations or combinations of one or more of the same. In one example, each of the steps shown in FIG. 9 may represent an algorithm whose structure includes and/or is represented by multiple sub-steps, examples of which will be provided in greater detail below.

As illustrated in FIG. 9, at step 902 one or more of the systems described herein may decompress the compressed 3D volumetric image data using the compression scheme. For example, restoring module 310 may, as part of computing device 402 and/or server 406 in FIG. 4, may decompress compressed 3D volumetric image data 326 into restored 3D volumetric image data 328.

In some examples, the orthodontic practitioner may send compressed 3D volumetric image data 326 from computing device 402 to server 406, which may be, for instance, a cloud server, a laboratory server, an external storage device, etc. Server 406 may decompress compressed 3D volumetric image data 326. In some examples, computing device 402 may send the compression scheme to server 406. In other examples, the compression scheme may be predetermined.

At step 904 one or more of the systems described herein may restore, from the decompressed 3D volumetric image data, image data previously modified for preparing the pre-processed 3D volumetric image data to produce restored 3D volumetric image data. For example, restoring module 310 may, as part of computing device 402 and/or server 406 in FIG. 4, restore restored 3D volumetric image data 328 by reverting modifications of pre-processed 3D volumetric image data 324 to 3D volumetric image data 322.

Figures 10A, 10B:
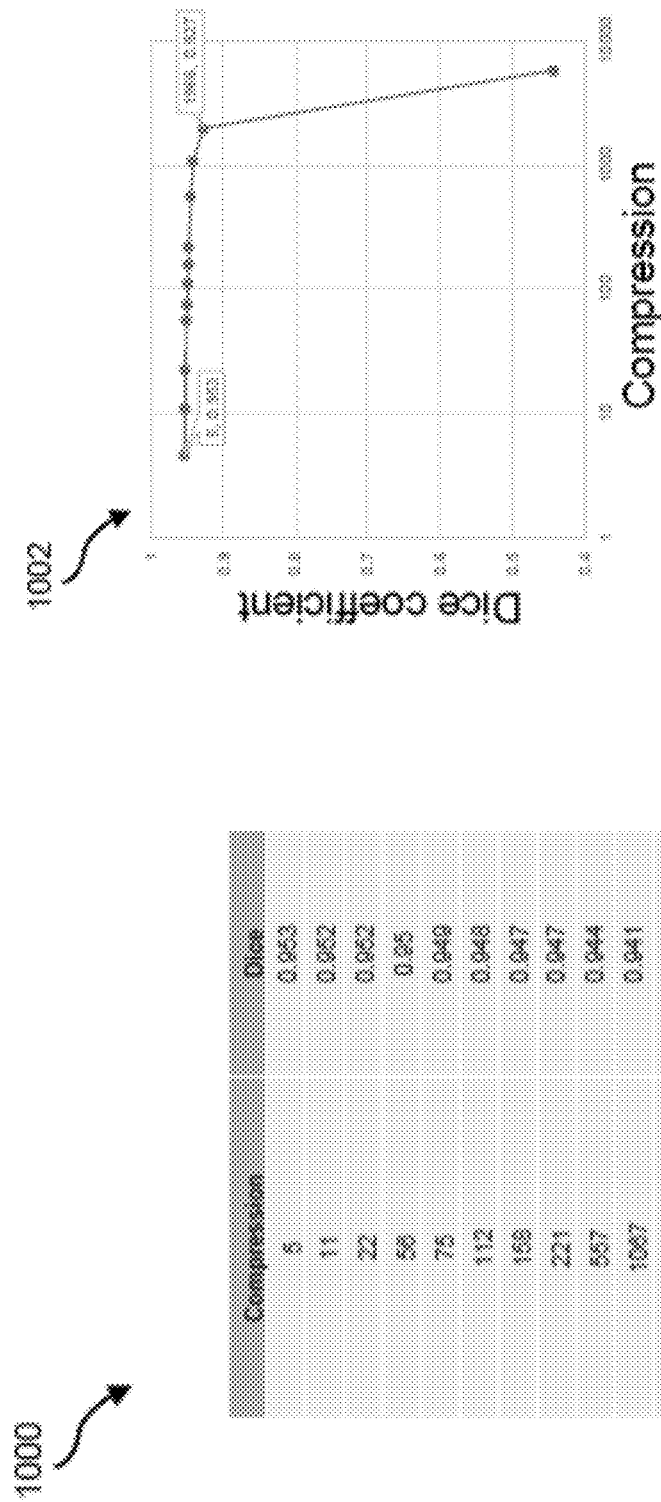
FIGS. 10A and 10B show a table and a graph of compression metrics, in accordance with some examples.

Restored 3D volumetric image data 328 may preserve information from 3D volumetric image data 322. In some examples, 3D volumetric image data 322 may comprise a first spatial resolution and restored 3D volumetric image data 328 may comprise a second spatial resolution. The first spatial resolution may match the second spatial resolution. A DICE score or coefficient between 3D volumetric image data 322 and restored 3D volumetric image data 328 may measure a similarity between original and decompressed data. The DICE score will be known to one of ordinary skill in the art and the DICE score is sometimes referred to as a Sørensen-Dice coefficient. The DICE score generally corresponds to the volume overlap of structures, for example, the volumetric overlap of one or more teeth. For example, the relevant (e.g., segmented) region from 3D volumetric image data 322 may be compared to the same region from restored 3D volumetric image data 328. FIG. 10A illustrates a table 1000 of DICE coefficients for a given compression rate. FIG. 10B illustrates a corresponding graph 1002. As seen in FIGS. 10A-B, a compression rate of up to about 2000 may yield sufficient similarity (e.g. from about 0.90 to about 0.95), whereas a compression rate of almost 6000 may produce unusable results.

In some examples, a compression rate of about 200 may be used. A higher compression rate may create additional processing overhead without significant gain in preserving data. By compressing the 3D volumetric image data, the compressed 3D volumetric image data may be more easily transferred, for instance requiring less bandwidth to transmit.

Figure 11A:
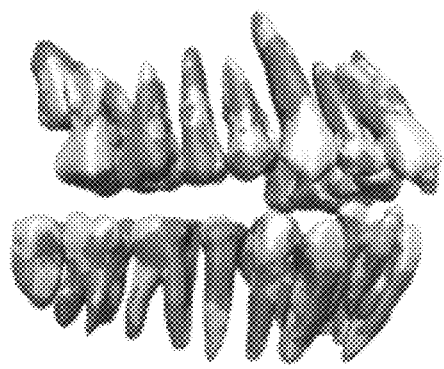
FIGS. 11A and 11B show visual comparisons of compression results, in accordance with some examples.
Figure 11B:
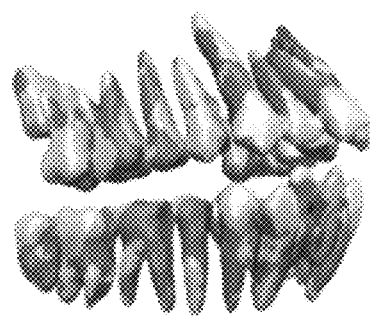

FIG. 11A illustrates a reconstruction 1100 with a 5× compression rate. FIG. 11B illustrates a reconstruction 1102 with an approximately 2000× compression rate. The shaded portions may correspond to restored data whereas the white portions may correspond to original uncompressed data. As shown by the visual comparison of FIGS. 11A-B, after the compression and restoration, the preserved data is significant enough for successful reconstruction.

In some examples, 3D volumetric image data 322 may comprise a plurality of teeth and compressed 3D volumetric image data 326 may comprise the plurality of teeth. A compression ratio of 3D volumetric image data 322 to compressed 3D image data 326 may comprise a value within a range from about 50 to about 2000. A DICE score from the plurality of teeth of 3D volumetric image data 322 compared to compressed 3D volumetric image data 326 may be within a range from about 0.95 to about 0.90.

In some examples, 3D volumetric image data 322 may comprises one or more segmentable tissue structures and compressed 3D volumetric image data 326 may comprise the one or more segmentable tissue structures. Each of the one or more segmentable tissue structures may comprise an outer surface enclosing an interior of the one or more segmentable tissue structures. A compression ratio of 3D volumetric image data 322 to the compressed 3D image data 326 may comprise a value within a range from about 50 to about 2000. A voxel overlap for the one or more segmentable tissue structures of 3D volumetric image data 322 compared to compressed 3D volumetric image data 326 may be within a range from about 0.95 to about 0.90.

In some examples, restoring module 310 may, as part of computing device 402 and/or server 406 in FIG. 4, perform segmentation to isolate a relevant structure from restored 3D volumetric image data 328. Restored volumetric image data 328 may comprise a plurality of voxels each encoded into one of empty space, soft tissue, bone or tooth. The relevant structure may be isolated based on an encoding of each of the plurality of voxels. In some examples, the relevant structure may comprise an individual tooth structure.

Figure 12:
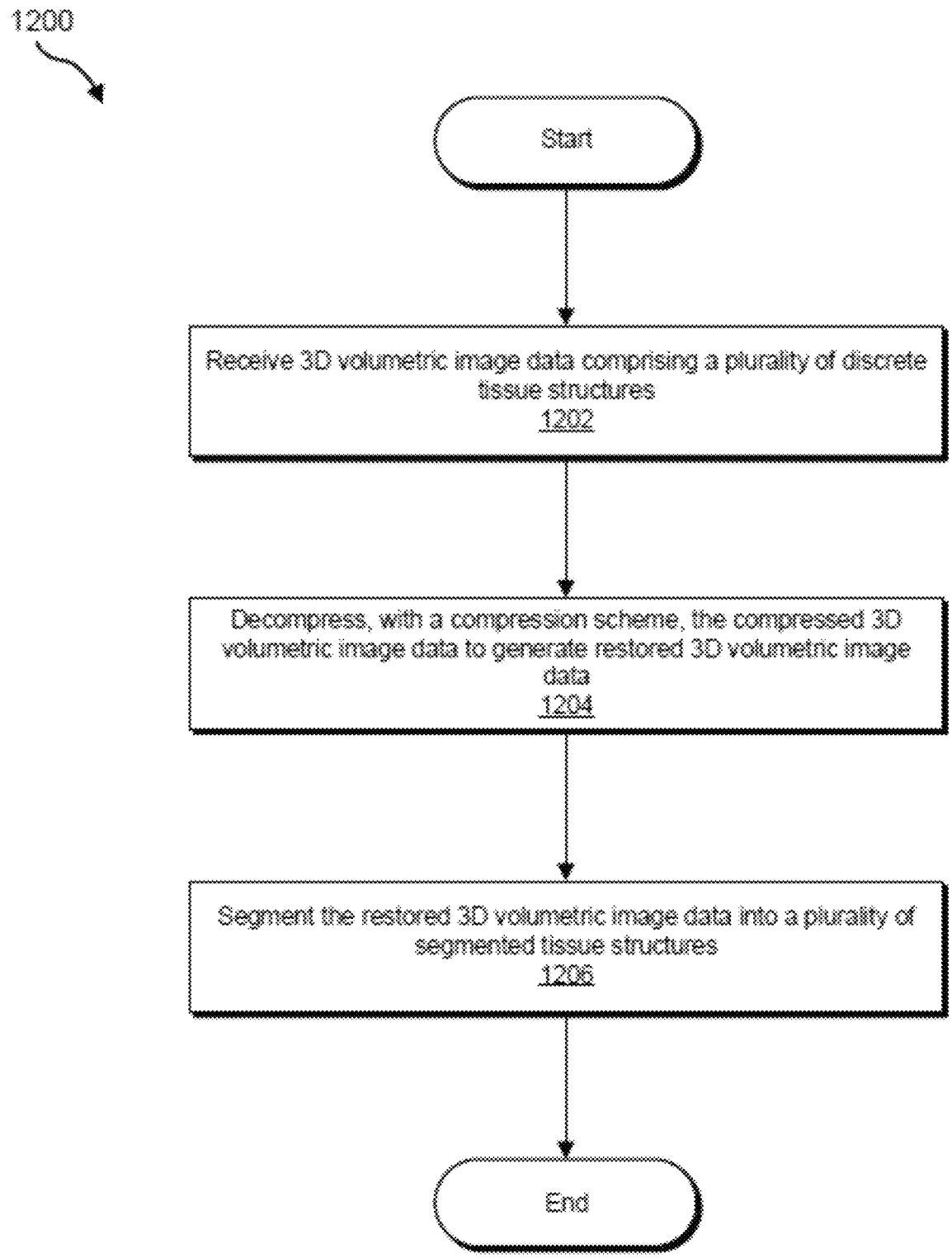
FIG. 12 shows a flow diagram of an example method of extracting data from compressed volumetric image data, in accordance with some examples.

FIG. 12 is a flow diagram of an example computer-implemented method 1200 for extracting medical imaging data from compressed data. The steps shown in FIG. 12 may be performed by any suitable computer-executable code and/or computing system, including system 300 in FIG. 3, system 400 in FIG. 4, and/or variations or combinations of one or more of the same. In one example, each of the steps shown in FIG. 12 may represent an algorithm whose structure includes and/or is represented by multiple sub-steps, examples of which will be provided in greater detail below.

As illustrated in FIG. 12, at step 1202 one or more of the systems described herein may receive 3D volumetric image data comprising a plurality of discrete tissue structures. For example, receiving module 304 may, as part of computing device 402 and/or server 406 in FIG. 4, may receive compressed 3D volumetric image data 326. Compressed 3D volumetric image data 326 may include various discrete tissue structures. For example, compressed 3D volumetric image data 326 may have been generated from raw 3D volumetric image data (e.g., 3D volumetric image data 322) comprising a plurality of teeth such that compressed 3D volumetric image data 326 comprises the plurality of teeth. A compression ratio of the raw 3D volumetric image data to the compressed 3D image data may comprise a value within a range from about 50 to about 2000 and a DICE score from the plurality of teeth of the raw 3D volumetric image data compared to the restored 3D volumetric image data may be within a range from about 0.95 to about 0.90.

In another example, the compressed 3D volumetric image data may have been generated from raw 3D volumetric image data comprising one or more segmentable tissue structures and the compressed 3D volumetric image data may comprise the one or more segmentable tissue structures. Each of the one or more segmentable tissue structures may comprise an outer surface enclosing an interior of the one or more segmentable tissue structures. A compression ratio of the raw 3D volumetric image data to the compressed 3D image data may comprise a value within a range from about 50 to about 2000. A voxel overlap for the one or more segmentable tissue structures of the raw 3D volumetric image data compared to the compressed 3D volumetric image data may be within a range from about 0.95 to about 0.90.

In yet another example, the compressed 3D volumetric image data may be generated from raw 3D volumetric image data comprising a first spatial resolution. The restored 3D volumetric image data may comprise a second spatial resolution matching the first spatial resolution. The raw 3D volumetric image data may comprise a dynamic range greater than 8 bits and the restored volumetric image data may comprise a dynamic range within a range from 2 bits per voxel to 8 bits per voxel.

As illustrated in FIG. 12, at step 1204 one or more of the systems described herein may decompress, with a compression scheme, the compressed 3D volumetric image data to generate restored 3D volumetric image data. For example, restoring module 310 may, as part of computing device 402 and/or server 406 in FIG. 4, decompress compressed 3D volumetric image data 326 into restored 3D volumetric image data 328.

At step 1206 one or more of the systems described herein may segment the restored 3D volumetric image data into a plurality of segmented tissue structures. For example, restoring module 310 may, as part of computing device 402 and/or server 406 in FIG. 4, segment restored 3D volumetric image data 328 into various segmented tissue structures, such as seen in FIGS. 2, 11A, and 11B.

In some examples, restoring module 310 may, as part of computing device 402 and/or server 406 restore, from the decompressed 3D volumetric image data, image data previously modified for preparing the pre-processed 3D volumetric image data to produce the restored 3D volumetric image data.

Although the systems and methods are described above with respect to orthodontic treatment, in other implementations, the anonymization methods and apparatus may be used for other medical contexts, such as plastic surgery. Alternatively, the anonymization methods and apparatus may be used outside of medical contexts, such as for generating avatars, concealing minors' identities for publishing, etc. In such contexts, the clinically relevant region may correspond to or be defined by important body features relevant to the given context.

Figure 13:
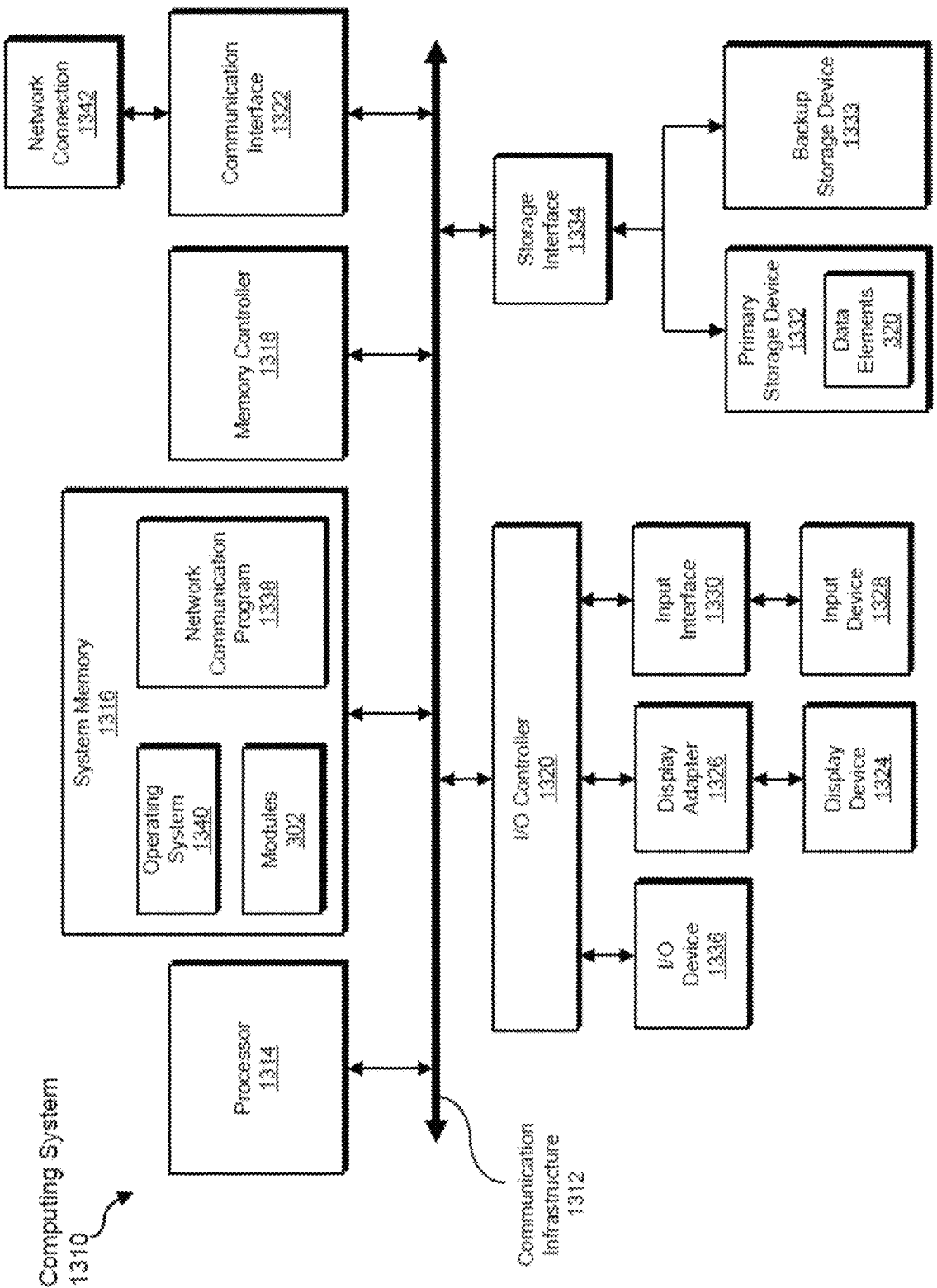
FIG. 13 shows a block diagram of an example computing system capable of implementing one or more examples described and/or illustrated herein, in accordance with some examples.

FIG. 13 is a block diagram of an example computing system 1310 capable of implementing one or more of the examples described and/or illustrated herein. For example, all or a portion of computing system 1310 may perform and/or be a means for performing, either alone or in combination with other elements, one or more of the steps described herein (such as one or more of the steps illustrated in FIG. 5). All or a portion of computing system 1310 may also perform and/or be a means for performing any other steps, methods, or processes described and/or illustrated herein.

Computing system 1310 broadly represents any single or multi-processor computing device or system capable of executing computer-readable instructions. Examples of computing system 1310 include, without limitation, workstations, laptops, client-side terminals, servers, distributed computing systems, handheld devices, or any other computing system or device. In its most basic configuration, computing system 1310 may include at least one processor 1314 and a system memory 1316.

Processor 1314 generally represents any type or form of physical processing unit (e.g., a hardware-implemented central processing unit) capable of processing data or interpreting and executing instructions. In certain examples, processor 1314 may receive instructions from a software application or module. These instructions may cause processor 1314 to perform the functions of one or more of the examples described and/or illustrated herein.

System memory 1316 generally represents any type or form of volatile or non-volatile storage device or medium capable of storing data and/or other computer-readable instructions. Examples of system memory 1316 include, without limitation, Random Access Memory (RAM), Read Only Memory (ROM), flash memory, or any other suitable memory device. Although not required, in certain examples computing system 1310 may include both a volatile memory unit (such as, for example, system memory 1316) and a non-volatile storage device (such as, for example, primary storage device 1332, as described in detail below). In one example, one or more of modules 302 from FIG. 3 may be loaded into system memory 1316.

In some examples, system memory 1316 may store and/or load an operating system 1340 for execution by processor 1314. In one example, operating system 1340 may include and/or represent software that manages computer hardware and software resources and/or provides common services to computer programs and/or applications on computing system 1310. Examples of operating system 1340 include, without limitation, LINUX, JUNOS, MICROSOFT WINDOWS, WINDOWS MOBILE, MAC OS, APPLE'S IOS, UNIX, GOOGLE CHROME OS, GOOGLE'S ANDROID, SOLARIS, variations of one or more of the same, and/or any other suitable operating system.

In certain examples, example computing system 1310 may also include one or more components or elements in addition to processor 1314 and system memory 1316. For example, as illustrated in FIG. 13, computing system 1310 may include a memory controller 1318, an Input/Output (I/O) controller 1320, and a communication interface 1322, each of which may be interconnected via a communication infrastructure 1312. Communication infrastructure 1312 generally represents any type or form of infrastructure capable of facilitating communication between one or more components of a computing device. Examples of communication infrastructure 1312 include, without limitation, a communication bus (such as an Industry Standard Architecture (ISA), Peripheral Component Interconnect (PCI), PCI Express (PCIe), or similar bus) and a network.

Memory controller 1318 generally represents any type or form of device capable of handling memory or data or controlling communication between one or more components of computing system 1310. For example, in certain examples, memory controller 1318 may control communication between processor 1314, system memory 1316, and I/O controller 1320 via communication infrastructure 1312.

I/O controller 1320 generally represents any type or form of module capable of coordinating and/or controlling the input and output functions of a computing device. For example, in certain examples I/O controller 1320 may control or facilitate transfer of data between one or more elements of computing system 1310, such as processor 1314, system memory 1316, communication interface 1322, display adapter 1326, input interface 1330, and storage interface 1334.

As illustrated in FIG. 13, computing system 1310 may also include at least one display device 1324 coupled to I/O controller 1320 via a display adapter 1326. Display device 1324 generally represents any type or form of device capable of visually displaying information forwarded by display adapter 1326. Similarly, display adapter 1326 generally represents any type or form of device configured to forward graphics, text, and other data from communication infrastructure 1312 (or from a frame buffer, as known in the art) for display on display device 1324.

As illustrated in FIG. 13, example computing system 1310 may also include at least one input device 1328 coupled to I/O controller 1320 via an input interface 1330. Input device 1328 generally represents any type or form of input device capable of providing input, either computer or human generated, to example computing system 1310. Examples of input device 1328 include, without limitation, a keyboard, a pointing device, a speech recognition device, variations or combinations of one or more of the same, and/or any other input device.

Additionally or alternatively, example computing system 1310 may include additional I/O devices. For example, example computing system 1310 may include I/O device 1336. In this example, I/O device 1336 may include and/or represent a user interface that facilitates human interaction with computing system 1310. Examples of I/O device 1336 include, without limitation, a computer mouse, a keyboard, a monitor, a printer, a modem, a camera, a scanner, a microphone, a touchscreen device, variations or combinations of one or more of the same, and/or any other I/O device.

Communication interface 1322 broadly represents any type or form of communication device or adapter capable of facilitating communication between example computing system 1310 and one or more additional devices. For example, in certain examples communication interface 1322 may facilitate communication between computing system 1310 and a private or public network including additional computing systems. Examples of communication interface 1322 include, without limitation, a wired network interface (such as a network interface card), a wireless network interface (such as a wireless network interface card), a modem, and any other suitable interface. In at least one example, communication interface 1322 may provide a direct connection to a remote server via a direct link to a network, such as the Internet. Communication interface 1322 may also indirectly provide such a connection through, for example, a local area network (such as an Ethernet network), a personal area network, a telephone or cable network, a cellular telephone connection, a satellite data connection, or any other suitable connection.

In certain examples, communication interface 1322 may also represent a host adapter configured to facilitate communication between computing system 1310 and one or more additional network or storage devices via an external bus or communications channel. Examples of host adapters include, without limitation, Small Computer System Interface (SCSI) host adapters, Universal Serial Bus (USB) host adapters, Institute of Electrical and Electronics Engineers (IEEE) 1394 host adapters, Advanced Technology Attachment (ATA), Parallel ATA (PATA), Serial ATA (SATA), and External SATA (eSATA) host adapters, Fibre Channel interface adapters, Ethernet adapters, or the like. Communication interface 1322 may also allow computing system 1310 to engage in distributed or remote computing. For example, communication interface 1322 may receive instructions from a remote device or send instructions to a remote device for execution.

In some examples, system memory 1316 may store and/or load a network communication program 1338 for execution by processor 1314. In one example, network communication program 1338 may include and/or represent software that enables computing system 1310 to establish a network connection 1342 with another computing system (not illustrated in FIG. 13) and/or communicate with the other computing system by way of communication interface 1322. In this example, network communication program 1338 may direct the flow of outgoing traffic that is sent to the other computing system via network connection 1342. Additionally or alternatively, network communication program 1338 may direct the processing of incoming traffic that is received from the other computing system via network connection 1342 in connection with processor 1314.

Although not illustrated in this way in FIG. 13, network communication program 1338 may alternatively be stored and/or loaded in communication interface 1322. For example, network communication program 1338 may include and/or represent at least a portion of software and/or firmware that is executed by a processor and/or Application Specific Integrated Circuit (ASIC) incorporated in communication interface 1322.

As illustrated in FIG. 13, example computing system 1310 may also include a primary storage device 1332 and a backup storage device 1333 coupled to communication infrastructure 1312 via a storage interface 1334. Storage devices 1332 and 1333 generally represent any type or form of storage device or medium capable of storing data and/or other computer-readable instructions. For example, storage devices 1332 and 1333 may be a magnetic disk drive (e.g., a so-called hard drive), a solid state drive, a floppy disk drive, a magnetic tape drive, an optical disk drive, a flash drive, or the like. Storage interface 1334 generally represents any type or form of interface or device for transferring data between storage devices 1332 and 1333 and other components of computing system 1310. In one example, data elements 320 from FIG. 3 may be stored and/or loaded in primary storage device 1332.

In certain examples, storage devices 1332 and 1333 may be configured to read from and/or write to a removable storage unit configured to store computer software, data, or other computer-readable information. Examples of suitable removable storage units include, without limitation, a floppy disk, a magnetic tape, an optical disk, a flash memory device, or the like. Storage devices 1332 and 1333 may also include other similar structures or devices for allowing computer software, data, or other computer-readable instructions to be loaded into computing system 1310. For example, storage devices 1332 and 1333 may be configured to read and write software, data, or other computer-readable information. Storage devices 1332 and 1333 may also be a part of computing system 1310 or may be a separate device accessed through other interface systems.

Many other devices or subsystems may be connected to computing system 1310. Conversely, all of the components and devices illustrated in FIG. 13 need not be present to practice the examples described and/or illustrated herein. The devices and subsystems referenced above may also be interconnected in different ways from that shown in FIG. 13. Computing system 1310 may also employ any number of software, firmware, and/or hardware configurations. For example, one or more of the examples disclosed herein may be encoded as a computer program (also referred to as computer software, software applications, computer-readable instructions, or computer control logic) on a computer-readable medium. The term "computer-readable medium," as used herein, generally refers to any form of device, carrier, or medium capable of storing or carrying computer-readable instructions. Examples of computer-readable media include, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

The computer-readable medium containing the computer program may be loaded into computing system 1310. All or a portion of the computer program stored on the computer-readable medium may then be stored in system memory 1316 and/or various portions of storage devices 1332 and 1333. When executed by processor 1314, a computer program loaded into computing system 1310 may cause processor 1314 to perform and/or be a means for performing the functions of one or more of the examples described and/or illustrated herein. Additionally or alternatively, one or more of the examples described and/or illustrated herein may be implemented in firmware and/or hardware. For example, computing system 1310 may be configured as an Application Specific Integrated Circuit (ASIC) adapted to implement one or more of the examples disclosed herein.

Figure 14:
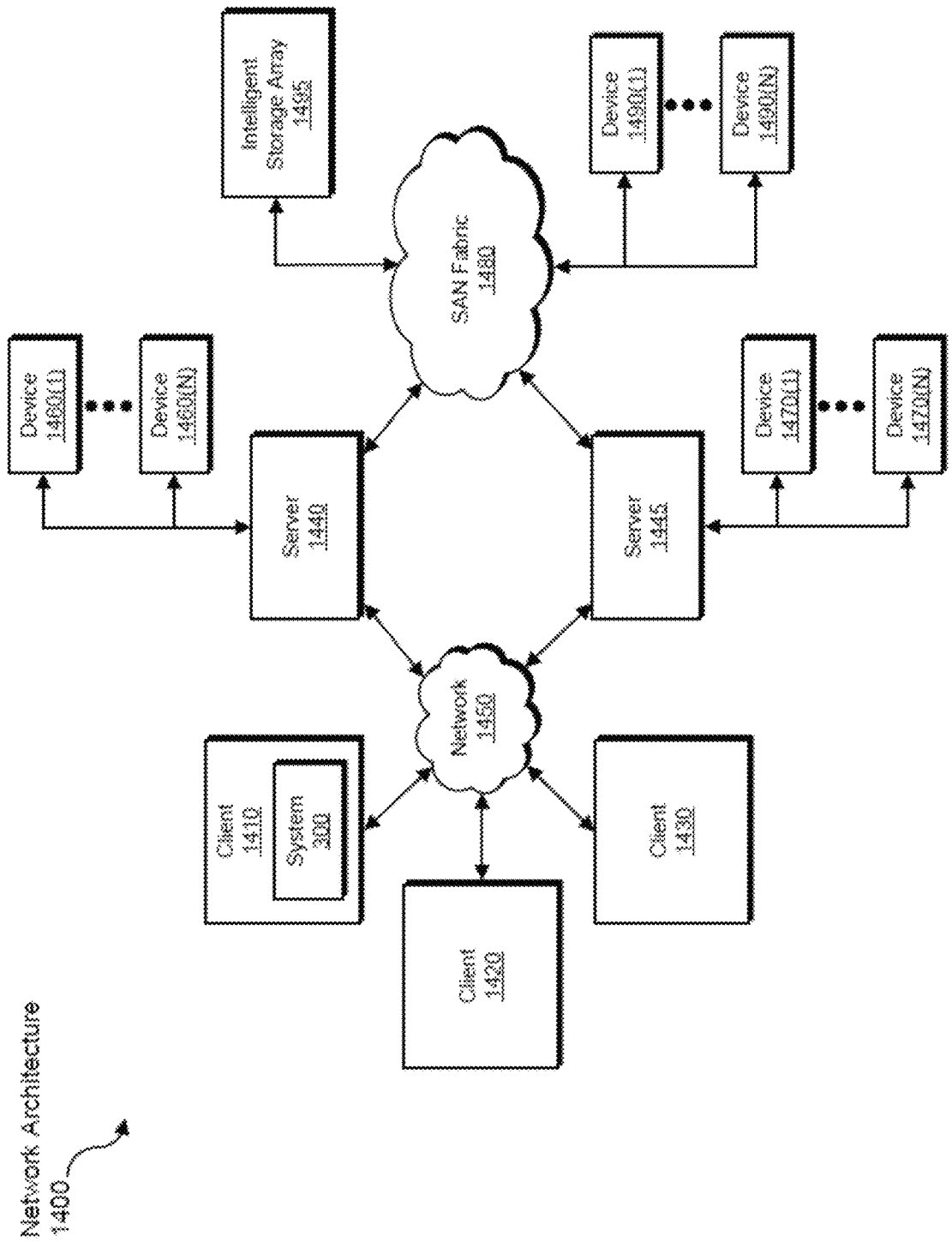
FIG. 14 shows a block diagram of an example computing network capable of implementing one or more of the examples described and/or illustrated herein, in accordance with some examples.

FIG. 14 is a block diagram of an example network architecture 1400 in which client systems 1410, 1420, and 1430 and servers 1440 and 1445 may be coupled to a network 1450. As detailed above, all or a portion of network architecture 1400 may perform and/or be a means for performing, either alone or in combination with other elements, one or more of the steps disclosed herein (such as one or more of the steps illustrated in FIG. 5). All or a portion of network architecture 1400 may also be used to perform and/or be a means for performing other steps and features set forth in the instant disclosure.

Client systems 1410, 1420, and 1430 generally represent any type or form of computing device or system, such as example computing system 1310 in FIG. 13. Similarly, servers 1440 and 1445 generally represent computing devices or systems, such as application servers or database servers, configured to provide various database services and/or run certain software applications. Network 1450 generally represents any telecommunication or computer network including, for example, an intranet, a WAN, a LAN, a PAN, or the Internet. In one example, client systems 1410, 1420, and/or 1430 and/or servers 1440 and/or 1445 may include all or a portion of system 300 from FIG. 3.

As illustrated in FIG. 14, one or more storage devices 1460(1)-(N) may be directly attached to server 1440. Similarly, one or more storage devices 1470(1)-(N) may be directly attached to server 1445. Storage devices 1460(1)-(N) and storage devices 1470(1)-(N) generally represent any type or form of storage device or medium capable of storing data and/or other computer-readable instructions. In certain examples, storage devices 1460(1)-(N) and storage devices 1470(1)-(N) may represent Network-Attached Storage (NAS) devices configured to communicate with servers 1440 and 1445 using various protocols, such as Network File System (NFS), Server Message Block (SMB), or Common Internet File System (CIFS).

Servers 1440 and 1445 may also be connected to a Storage Area Network (SAN) fabric 1480. SAN fabric 1480 generally represents any type or form of computer network or architecture capable of facilitating communication between a plurality of storage devices. SAN fabric 1480 may facilitate communication between servers 1440 and 1445 and a plurality of storage devices 1490(1)-(N) and/or an intelligent storage array 1495. SAN fabric 1480 may also facilitate, via network 1450 and servers 1440 and 1445, communication between client systems 1410, 1420, and 1430 and storage devices 1490(1)-(N) and/or intelligent storage array 1495 in such a manner that devices 1490(1)-(N) and array 1495 appear as locally attached devices to client systems 1410, 1420, and 1430. As with storage devices 1460(1)-(N) and storage devices 1470(1)-(N), storage devices 1490(1)-(N) and intelligent storage array 1495 generally represent any type or form of storage device or medium capable of storing data and/or other computer-readable instructions.

In certain examples, and with reference to example computing system 1310 of FIG. 13, a communication interface, such as communication interface 1322 in FIG. 13, may be used to provide connectivity between each client system 1410, 1420, and 1430 and network 1450. Client systems 1410, 1420, and 1430 may be able to access information on server 1440 or 1445 using, for example, a web browser or other client software. Such software may allow client systems 1410, 1420, and 1430 to access data hosted by server 1440, server 1445, storage devices 1460(1)-(N), storage devices 1470(1)-(N), storage devices 1490(1)-(N), or intelligent storage array 1495. Although FIG. 14 depicts the use of a network (such as the Internet) for exchanging data, the examples described and/or illustrated herein are not limited to the Internet or any particular network-based environment.

In at least one example, all or a portion of one or more of the examples disclosed herein may be encoded as a computer program and loaded onto and executed by server 1440, server 1445, storage devices 1460(1)-(N), storage devices 1470(1)-(N), storage devices 1490(1)-(N), intelligent storage array 1495, or any combination thereof. All or a portion of one or more of the examples disclosed herein may also be encoded as a computer program, stored in server 1440, run by server 1445, and distributed to client systems 1410, 1420, and 1430 over network 1450.

As detailed above, computing system 1310 and/or one or more components of network architecture 1400 may perform and/or be a means for performing, either alone or in combination with other elements, one or more steps of an example method for compressing and extracting medical imaging data.

While the foregoing disclosure sets forth various examples using specific block diagrams, flowcharts, and examples, each block diagram component, flowchart step, operation, and/or component described and/or illustrated herein may be implemented, individually and/or collectively, using a wide range of hardware, software, or firmware (or any combination thereof) configurations. In addition, any disclosure of components contained within other components should be considered example in nature since many other architectures can be implemented to achieve the same functionality.

In some examples, all or a portion of example system 300 in FIG. 3 may represent portions of a cloud-computing or network-based environment. Cloud-computing environments may provide various services and applications via the Internet. These cloud-based services (e.g., software as a service, platform as a service, infrastructure as a service, etc.) may be accessible through a web browser or other remote interface. Various functions described herein may be provided through a remote desktop environment or any other cloud-based computing environment.

In various examples, all or a portion of example system 300 in FIG. 3 may facilitate multi-tenancy within a cloud-based computing environment. In other words, the software modules described herein may configure a computing system (e.g., a server) to facilitate multi-tenancy for one or more of the functions described herein. For example, one or more of the software modules described herein may program a server to enable two or more clients (e.g., customers) to share an application that is running on the server. A server programmed in this manner may share an application, operating system, processing system, and/or storage system among multiple customers (i.e., tenants). One or more of the modules described herein may also partition data and/or configuration information of a multi-tenant application for each customer such that one customer cannot access data and/or configuration information of another customer.

According to various examples, all or a portion of example system 300 in FIG. 3 may be implemented within a virtual environment. For example, the modules and/or data described herein may reside and/or execute within a virtual machine. As used herein, the term "virtual machine" generally refers to any operating system environment that is abstracted from computing hardware by a virtual machine manager (e.g., a hypervisor). Additionally or alternatively, the modules and/or data described herein may reside and/or execute within a virtualization layer. As used herein, the term "virtualization layer" generally refers to any data layer and/or application layer that overlays and/or is abstracted from an operating system environment. A virtualization layer may be managed by a software virtualization solution (e.g., a file system filter) that presents the virtualization layer as though it were part of an underlying base operating system. For example, a software virtualization solution may redirect calls that are initially directed to locations within a base file system and/or registry to locations within a virtualization layer.

In some examples, all or a portion of example system 300 in FIG. 3 may represent portions of a mobile computing environment. Mobile computing environments may be implemented by a wide range of mobile computing devices, including mobile phones, tablet computers, e-book readers, personal digital assistants, wearable computing devices (e.g., computing devices with a head-mounted display, smartwatches, etc.), and the like. In some examples, mobile computing environments may have one or more distinct features, including, for example, reliance on battery power, presenting only one foreground application at any given time, remote management features, touchscreen features, location and movement data (e.g., provided by Global Positioning Systems, gyroscopes, accelerometers, etc.), restricted platforms that restrict modifications to system-level configurations and/or that limit the ability of third-party software to inspect the behavior of other applications, controls to restrict the installation of applications (e.g., to only originate from approved application stores), etc. Various functions described herein may be provided for a mobile computing environment and/or may interact with a mobile computing environment.

In addition, all or a portion of example system 300 in FIG. 3 may represent portions of, interact with, consume data produced by, and/or produce data consumed by one or more systems for information management. As used herein, the term "information management" may refer to the protection, organization, and/or storage of data. Examples of systems for information management may include, without limitation, storage systems, backup systems, archival systems, replication systems, high availability systems, data search systems, virtualization systems, and the like.

In some examples, all or a portion of example system 300 in FIG. 3 may represent portions of, produce data protected by, and/or communicate with one or more systems for information security. As used herein, the term "information security" may refer to the control of access to protected data. Examples of systems for information security may include, without limitation, systems providing managed security services, data loss prevention systems, identity authentication systems, access control systems, encryption systems, policy compliance systems, intrusion detection and prevention systems, electronic discovery systems, and the like.

The methods and apparatuses (e.g., systems, which may include software, hardware and/or firmware for executing the techniques described herein) may generally be used to compress large image data sets, such as (but not limited to) cone beam computed tomography image (CBCT), or a magnetic resonance imaging (MRI) data sets. As discussed above, such data sets may be extremely large and typical compression techniques are unable to compress them without significant loss of information and/or the introduction of artifacts. The methods and apparatuses described herein may provide up to 2000 fold compression (e.g., compression rate). These methods and apparatuses may greatly simplify the data transfer between, for example, the apparatus performing/collecting the imaging data, such as a doctor's CBCT scanner, and one or more other facilities (e.g., cloud, external laboratories, external storage etc.). These methods and apparatuses may also increase the speed of processing and analysis of the imaging data.

A difficulty in data transfer of CBCT data is the large amount of data in each CBCT scan, and uploading this data is time-consuming process. The methods and apparatuses described herein may provide a significant decrease in the amount of data to be sent without loss of essential information. In some examples, these methods or apparatuses may be integrated as part of the imaging system; in one example, these methods and apparatuses may be integrated as part of a CBCT scanner and/or as part of an in web-browser uploading page.

Figure 15A:
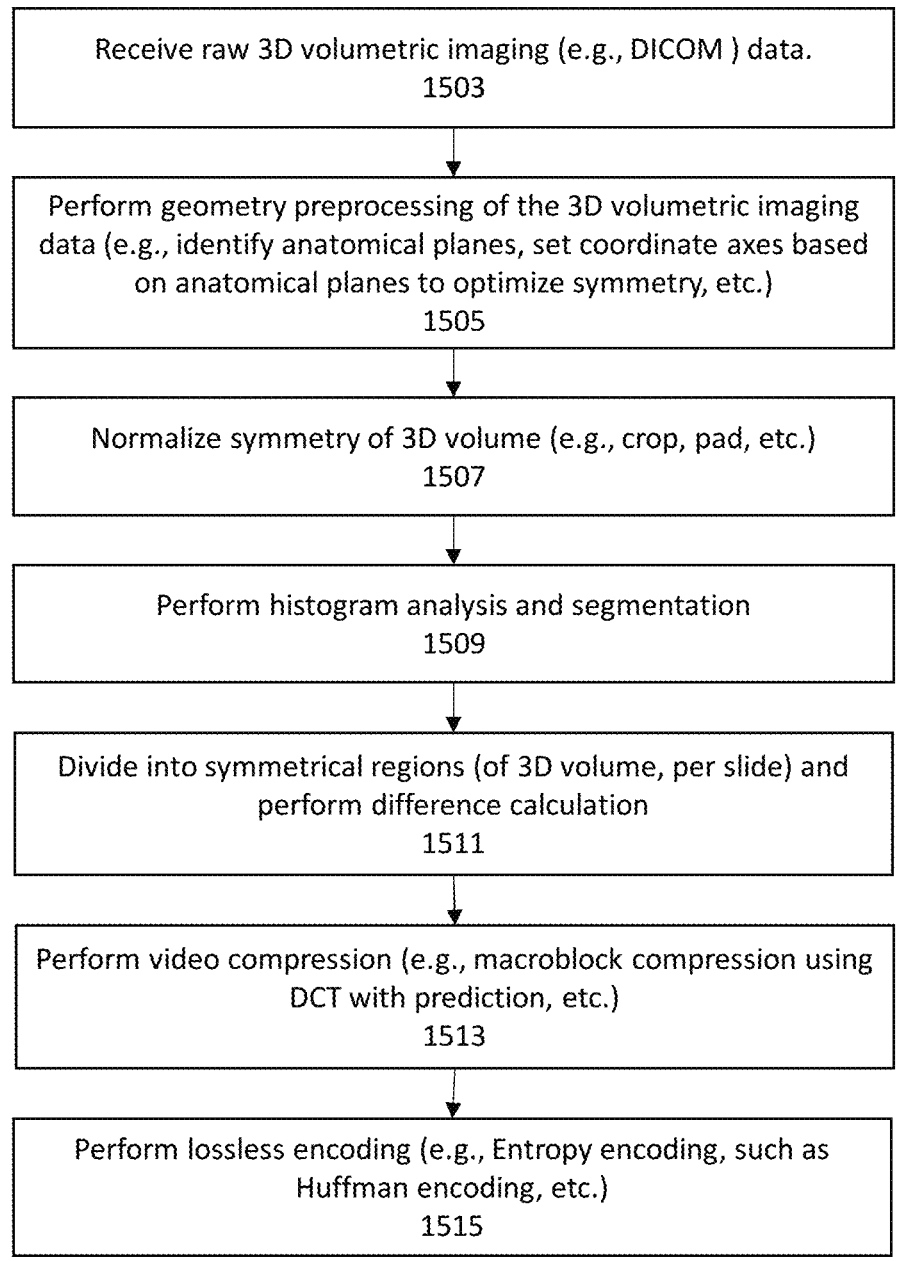
FIG. 15A shows a flow diagram of an example method for compression of (e.g., dense) 3D volumetric imaging data.

For example, FIG. 15A illustrates one example of a method of compressing a 3D volumetric image data set. The method may begin by receiving (e.g., in a processor) raw 3D volumetric image data (e.g., DICOM data) 1503. In some examples, these methods (and apparatuses for performing them) may include geometrically preprocessing the raw imaging data 1505. The geometric processing may include identifying anatomical planes from the raw data (e.g., DICOM standardized data), such as one or more of: sagittal, coronal, transverse, and/or axial planes. Once identified from the data, X, Y, and Z axes for the data set may be set for the data set to align with the anatomical planes. For example, the data set may be translated (e.g., rotated, shifted, etc.) so that they are parallel to X, Y and Z axes. Thus, the volume may initially be made more symmetric. The volume may then be cropped consistent with the new X, Y and Z axes to exclude empty regions 1507. In some cases the volume may be padded so that it has uniform sides (e.g., padded with empty space).

In some examples, a histogram analysis (e.g., of the dynamic range of the data set) may be performed to identify a region or subset within the dynamic range that includes the majority of the information from the imaging volume 1509. As mentioned above, imaging (e.g., DICOM) volumes may have a large dynamic range (e.g., up to or more than 16 bits per voxel). However, dental structures such as teeth, roots and bone reconstruction information is typically concentrated at lower regions within the dynamic range. Thus, the methods and apparatuses described herein may remove one or more portions of the dynamic range that do not include significant data (e.g., regions that include less useful data, such as dental data related to fillings, inlays, etc.), which may be highly reflective and therefore "bright."

In some examples the histogram analysis may reduce the dynamic range by segmenting the data into clinically relevant regions, such as anatomical regions and in particular dental categories. For example, clinically relevant regions (categories) may include bones, soft tissue, teeth crowns, teeth roots, etc. Each of these clinically relevant regions may be coded with a reference (e.g., a 4-8 bit number, such as 0 for empty space, 1 for soft tissue, 2 for bone, 3 for tooth, etc.). Thus, these methods and/or apparatuses may segment data (e.g., voxel data) using these clinically relevant (and in particular, dental-relevant) predefined categories. In some cases the apparatus may include a machine learning agent to segment (e.g., identify) the voxels.

In some examples, the revised uniform (and optionally cropped) volume may be analyzed to divide it into symmetric sections (e.g., halves, such as left/right halves) where the images are sufficiently similar. The method or apparatus may identify these symmetric regions 1511. Any of these method and apparatuses may then compare the identified symmetric region(s) to determine differences, e.g., differences based on the segmentation.

The pre-processed data (the modified 3D volume, modified as described above) may then be compressed using video compression 1513. For example, the 3D volume including the differences calculations may be compressed using macroblock compression, e.g., using a compression scheme such as a discrete cosine transformation (DCT) with prediction. Finally, the compressed data set may be encoded, e.g., using a lossless data compression scheme, such as entropy encoding (e.g., Huffman) 1515. As discussed and illustrated above, these techniques may provide highly accurate compression of up to 200 fold, without significant loss of information.

Any appropriate image data set may be used, including 3D volumetric data sets or video data sets. For example, CT scan data, which is similar to video sequence data, may be treated as volumetric data in which images of the same regions may be taken at different times. Thus, the scan data may be treated as a series of slices (e.g., series of thin image "slices") that may be processed and compressed as described herein. CT scans may be considered dense data sets, which may benefit in particular to the techniques described herein. A dense volume may include a sequence of 2D frames that are taken at different times; this data may be compressed as described herein. The preprocessing steps discussed above may align the data set and identify regions of symmetry that may then be used to simplify the dense data set, by identifying differences between symmetric regions. For example, left and right parts of a scanned body may be symmetric, after aligning the images and trimming (and/or padding) appropriately. For example, when imaging an image of a patient's head (e.g., jaw, teeth, etc.), the position of the subject's head may be estimated, and the X, Y, Z axes set from the data. The dataset may then be symmetrically cut on the left and right side. As mentioned above, the use of histogram analysis may be helpful to identify an accurate and useful dynamic range. Each voxel may be reduced to between 2 bits depth or 8 bits depth (e.g., from an initial 16 bits of depth).

In some examples, some depth information can be completely removed from the image data set. For example, as mentioned above, hard structures (e.g., highly reflective structures) such as details of inlays and/or metal fillings, etc. (or any metallic detail) may be included in the data set and may be very "bright" in the imaging data, which may lead to corruption of the dynamic range, by skewing it towards high-density/reflective values. As described above, the methods and apparatuses described herein may decrease the dynamic range to concentrate on anatomic features.

Any of the methods and apparatuses described herein may include compressing a static 3D volumetric data set using one or more video compression techniques by transforming the static 3D volumetric dataset into a series of two-dimensional images in a time sequence. Thus, the volumetric data set may be processed by treating the plurality of slices of through the 3D volumetric data set as a sequence of time points in a video loop to compress the volumetric data using video compression scheme. For example, a 3D volume may be compressed using a video compression technique, including after pre-processing as described above (e.g., by identify and/or setting an X, Y, Z axis, aligning and cropping and/or padding, adjusting the dynamic range, etc.) and then transforming one axis into a time axis, rather than a spatial axis.

Examples of video compression were described above, e.g., including using macroblock compression (e.g., using DCT) and/or using a video codec. The result may be compressed data.

Figure 15B:
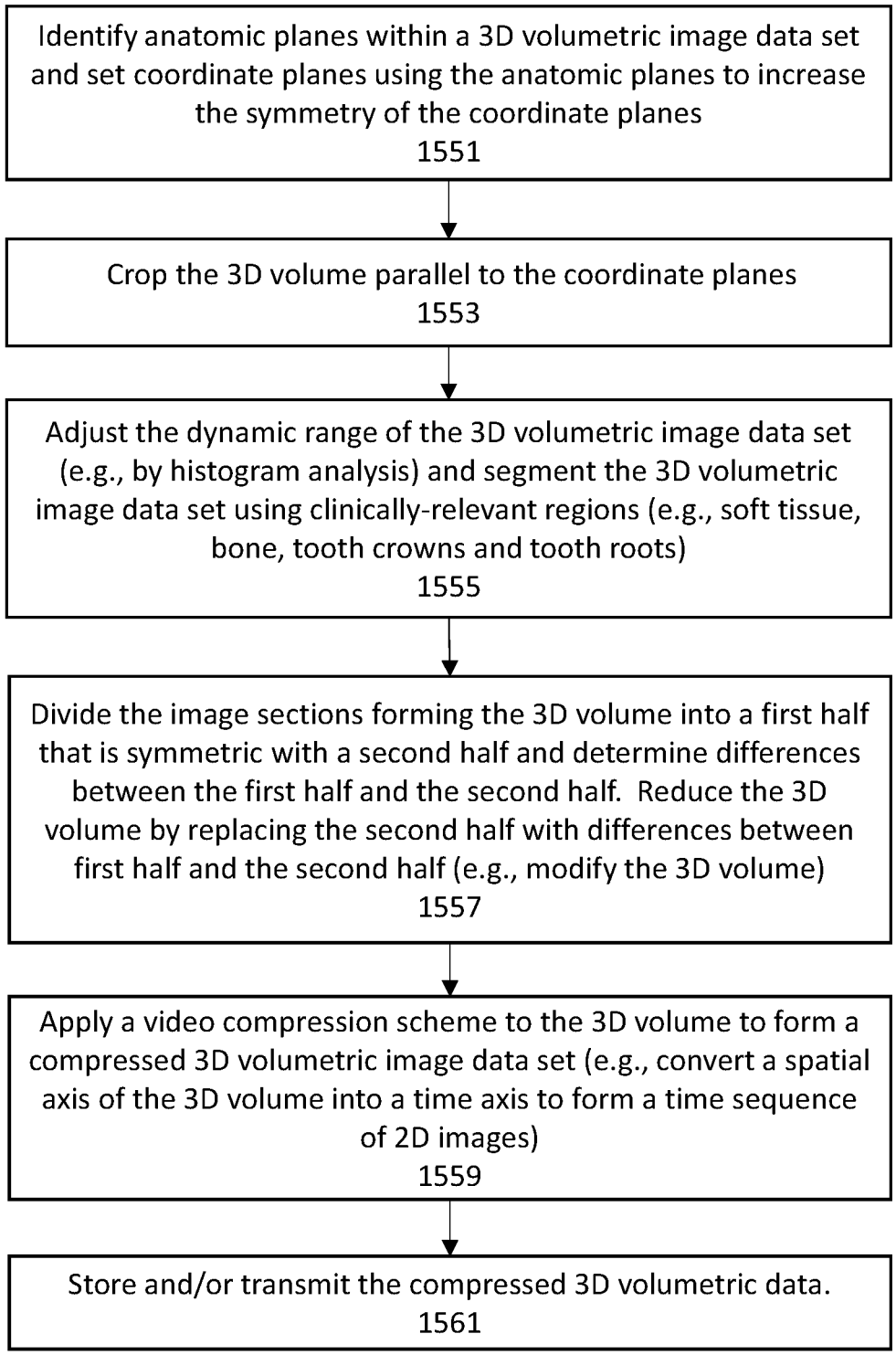
FIG. 15B shows another example of a flow diagram of an example method for compression of 3D volumetric imaging data.

FIG. 15B illustrates one example of a method of compressing dental imaging data as described herein, which may be a particular application of the more generic method of compressing 3D volumetric image data sets discussed above. In this example the method of compressing a three-dimensional (3D) volumetric image data set may optionally include receiving the 3D volumetric image data. The 3D volumetric image data may include a plurality of image sections (e.g., through a patient's jaw(s)), forming a 3D volume. The method may include identifying at least two anatomic planes within the 3D volumetric image data set and setting at least two coordinate planes using the at least two anatomic planes to increase the symmetry of the coordinate planes 1551. The method may further include cropping the 3D volume parallel to the coordinate planes 1553 and adjusting the dynamic range of the 3D volumetric image data set by histogram analysis and segmenting the 3D volumetric image data set using clinically-relevant regions comprising, for example: soft tissue, bone, tooth crowns and tooth roots 1555. The method may further include dividing the image sections forming the 3D volume into a first half that is symmetric with a second half, determining differences between the first half and the second half and reducing the 3D volume by replacing the second half with differences between first half and the second half 1557.

The pre-processed 3D volume may then be compressed by applying a video compression scheme to the 3D volume to form a compressed 3D volumetric image data set by converting a spatial axis of the 3D volume into a time axis to form a time sequence of 2D images 1559. The resulting compressed 3D volumetric image data set may then be stored and/or transmitted 1561.

The process parameters and sequence of steps described and/or illustrated herein are given by way of example only and can be varied as desired. For example, while the steps illustrated and/or described herein may be shown or discussed in a particular order, these steps do not necessarily need to be performed in the order illustrated or discussed. The various example methods described and/or illustrated herein may also omit one or more of the steps described or illustrated herein or include additional steps in addition to those disclosed.

While various examples have been described and/or illustrated herein in the context of fully functional computing systems, one or more of these examples may be distributed as a program product in a variety of forms, regardless of the particular type of computer-readable media used to actually carry out the distribution. The examples disclosed herein may also be implemented using software modules that perform certain tasks. These software modules may include script, batch, or other executable files that may be stored on a computer-readable storage medium or in a computing system. In some examples, these software modules may configure a computing system to perform one or more of the examples disclosed herein.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Graphics Processing Units (GPUs), Field-Programmable Gate Arrays (FPGAs) that implement softcore processors, Application-Specific Integrated Circuits (ASICs), portions of one or more of the same, variations or combinations of one or more of the same, or any other suitable physical processor.

Although illustrated as separate elements, the method steps described and/or illustrated herein may represent portions of a single application. In addition, in some examples one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

Examples of the present disclosure have been shown and described as set forth herein and are provided by way of example only. One of ordinary skill in the art will recognize numerous adaptations, changes, variations and substitutions without departing from the scope of the present disclosure. Several alternatives and combinations of the examples disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A system for compressing a three-dimensional (3D) volumetric image data set including a plurality of image sections forming a 3D volume, the system comprising:
    one or more processors;
    a memory coupled to the one or more processors, the memory storing computer-program instructions, that, when executed by the one or more processors, perform a computer-implemented method comprising:
        receiving a 3D volumetric image data set comprising a cone beam computed tomography (CBCT) data of a patient's dentition;
        identifying one or more anatomic planes within the 3D volumetric image data set and setting coordinate planes using the one or more anatomic planes;
        cropping the 3D volume parallel to the coordinate planes;
        adjusting a dynamic range of the cropped 3D volumetric image data set based on assigning values to each voxel of the 3D volumetric image data set based on a type of anatomical structure and corresponding four intensity values;
        converting a spatial axis of the dynamic range adjusted and cropped 3D volume into a time axis to form a time sequence of 2D images and applying a video compression scheme to the time sequence of 2D images to form a compressed 3D volumetric image data set;
        transmitting the compressed 3D volumetric image data set to a remote server;
        receiving, at the remote server, the compressed 3D volumetric image data set; and
        generating a restored 3D volumetric image data set based at least in part on the video compression scheme applied to the time sequence of 2D images.

2. The system of claim 1, wherein the computer-implemented method identifies the one or more anatomic planes within the 3D volumetric image data set and sets the coordinate planes to increase symmetry of the coordinate planes.

3. The system of claim 1, wherein the computer-implemented method crops the 3D volume parallel to the coordinate planes to minimize empty regions of the 3D volume.

4. The system of claim 1, wherein the computer-implemented method further comprises padding the 3D volume with empty regions to keep the 3D volume symmetrical after cropping.

5. The system of claim 1, wherein the computer-implemented method adjusts the dynamic range of the 3D volumetric image data set by histogram analysis.

6. The system of claim 1, wherein adjusting the dynamic range of the 3D volumetric image data set further includes reencoding voxels of the 3D volumetric image data based on the anatomical structure.

7. The system of claim 1, wherein adjusting the dynamic range of the 3D volumetric image data further includes segmenting the 3D volumetric data set using clinically-relevant regions comprising: soft tissue, bone, tooth crowns and tooth roots.

8. The system of claim 1, wherein the computer-implemented method further comprises dividing the image sections forming the 3D volume into a first half that is symmetric with a second half, determining differences between the first half and the second half and reducing the 3D volume by replacing the second half with differences between first half and the second half before converting the spatial axis of the 3D volume into the time axis.

9. The system of claim 1, further comprising an imaging device in communication with the one or more processors.

10. The system of claim 1, wherein the computer-implemented method further comprises storing or transmitting the compressed 3D volumetric image data set.

11. The system of claim 1, wherein the computer-implemented method applies the video compression scheme to the time sequence of 2D images to form the compressed 3D volumetric image data set at a compression rate of between 50 and 2500 times.

12. The system of claim 1, wherein the computer-implemented method applies the video compression scheme to the time sequence of 2D images to form the compressed 3D volumetric image data set at a compression rate of 50 times or more.

13. The system of claim 1, wherein the computer-implemented method applies the video compression scheme by applying macroblock compression using a discrete cosine transformation (DCT) to the time sequence of 2D images to form a compressed 3D volumetric image data set.

14. The system of claim 1, wherein the computer-implemented method further comprises encoding the compressed 3D volumetric image data set using entropy encoding.

15. A system for compressing a three-dimensional (3D) volumetric image data set including a plurality of image sections forming a 3D volume, the system comprising:
    one or more processors;
    a memory coupled to the one or more processors, the memory storing computer-program instructions, that, when executed by the one or more processors, perform a computer-implemented method comprising:
        receiving a 3D volumetric image data set comprising a cone beam computed tomography (CBCT) data of a patient's dentition;
        identifying at least two anatomic planes within the 3D volumetric image data set and setting at least two coordinate planes using the at least two anatomic planes to increase symmetry of the coordinate planes;
        cropping the 3D volume parallel to the coordinate planes;
        adjusting a dynamic range of the cropped 3D volumetric image data set based on assigning values to each voxel of the 3D volumetric image data set based on a type of anatomical structure and corresponding four intensity values;

dividing the image sections forming the dynamic range adjusted and cropped 3D volume into a first half that is symmetric with a second half, determining differences between the first half and the second half and reducing the 3D volume by replacing the second half with differences between first half and the second half;

applying a video compression scheme to the 3D volume to form a compressed 3D volumetric image data set by converting a spatial axis of the 3D volume into a time axis to form a time sequence of 2D images;

storing or transmitting the compressed 3D volumetric image data set to a remote server;

receiving at the remote server, the compressed 3D volumetric image data set; and generating a restored 3D volumetric image data set based at least in part on the video compression scheme applied to the time sequence of 2D images.

16. A method of compressing a three-dimensional (3D) volumetric image data set including a plurality of image sections forming a 3D volume, the method comprising:

receiving a 3D volumetric image data set comprising a cone beam computed tomography (CBCT) data of a patient's dentition;

identifying one or more anatomic planes within the 3D volumetric image data set and setting coordinate planes using the one or more anatomic planes;

cropping the 3D volume parallel to the coordinate planes;

adjusting a dynamic range of the cropped 3D volumetric image data set based on assigning values to each voxel of the 3D volumetric image data set based on a type of anatomical structure and corresponding four intensity values;

converting a spatial axis of the dynamic range adjusted and cropped 3D volume into a time axis to form a time sequence of 2D images and applying a video compression scheme to the time sequence of 2D images to form a compressed 3D volumetric image data set;

transmitting the compressed 3D volumetric image data set to a remote server;

receiving, at the remote server, the compressed 3D volumetric image data set; and generating a restored 3D volumetric image data set based at least in part on the video compression scheme applied to the time sequence of 2D images.

17. The method of claim 16, wherein identifying the one or more anatomic planes within the 3D volumetric image data set and setting the coordinate planes comprises setting the coordinate planes to increase symmetry of the coordinate planes.

18. The method of claim 16, further comprising cropping the 3D volume parallel to the coordinate planes to minimize empty regions of the 3D volume.

19. The method of claim 16, further comprising padding the 3D volume with empty regions to keep the 3D volume symmetrical after cropping.

20. The method of claim 16, wherein adjusting the dynamic range of the 3D volumetric image data set comprises adjusting by histogram analysis.

21. The method of claim 20, further comprising segmenting the 3D volumetric image data set using clinically-relevant regions.

22. The method of claim 21, wherein the clinically-relevant regions comprise: soft tissue, bone, tooth crowns and tooth roots.

23. The method of claim 16, further comprising dividing the image sections forming the 3D volume into a first half that is symmetric with a second half, determining differences between the first half and the second half, and reducing the 3D volume by replacing the second half with differences between first half and the second half before converting the spatial axis of the 3D volume into the time axis.

24. The method of claim 16, further comprising storing or transmitting the compressed 3D volumetric image data set.

25. The method of claim 16, wherein applying the video compression scheme to the time sequence of 2D images to form the compressed 3D volumetric image data set comprises forming the compressed 3D volumetric image data set at a compression rate of between 50 and 2500 times.

26. The method of claim 16, wherein applying the video compression scheme to the time sequence of 2D images to form the compressed 3D volumetric image data set comprises forming the compressed 3D volumetric image data set at a compression rate of 50 times or more.

27. The method of claim 16, wherein applying the video compression scheme to the time sequence of 2D images comprises applying macroblock compression using a discrete cosine transformation (DCT).

28. The method of claim 16, further comprising encoding the compressed 3D volumetric image data set using entropy encoding.

29. A method of compressing a three-dimensional (3D) volumetric image data set including a plurality of image sections forming a 3D volume, the method comprising:

receiving a 3D volumetric image data set comprising a cone beam computed tomography (CBCT) data of a patient's dentition;

identifying at least two anatomic planes within the 3D volumetric image data set and setting at least two coordinate planes using the at least two anatomic planes to increase symmetry of the coordinate planes;

cropping the 3D volume parallel to the coordinate planes;

adjusting a dynamic range of the cropped 3D volumetric image data set based on assigning values to each voxel of the 3D volumetric image data set based on a type of anatomical structure and corresponding four intensity values;

dividing the image sections forming the dynamic range adjusted and cropped 3D volume into a first half that is symmetric with a second half, determining differences between the first half and the second half and reducing the 3D volume by replacing the second half with differences between first half and the second half;

applying a video compression scheme to the 3D volume to form a compressed 3D volumetric image data set by converting a spatial axis of the 3D volume into a time axis to form a time sequence of 2D images; and storing or transmitting the compressed 3D volumetric image data set to a remote server;

receiving, at the remote server, the compressed 3D volumetric image data set; and generating a restored 3D volumetric image data set based at least in part on the video compression scheme applied to the time sequence of 2D images.

* * * * *